(12) United States Patent
Branch et al.

(10) Patent No.: US 12,084,708 B1
(45) Date of Patent: *Sep. 10, 2024

(54) ACOUSTIC WAVE RESONATOR WITH ACTIVE SHUNT CAPACITANCE CANCELLATION AND SYSTEMS THEREOF

(71) Applicant: National Technology & Engineering Solutions of Sandia, LLC, Albuquerque, NM (US)

(72) Inventors: Darren W. Branch, Albuquerque, NM (US); Bryan Carson, Tijeras, NM (US); DeAnna Marie Campbell, Albuquerque, NM (US); Kurt Wessendorf, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 982 days.

This patent is subject to a terminal disclaimer.

(21) Appl. No.: 17/088,221

(22) Filed: Nov. 3, 2020

Related U.S. Application Data

(60) Provisional application No. 62/932,297, filed on Nov. 7, 2019.

(51) Int. Cl.
*H03B 5/36* (2006.01)
*B01L 3/00* (2006.01)
(Continued)

(52) U.S. Cl.
CPC .......... *C12Q 1/18* (2013.01); *B01L 3/502715* (2013.01); *G01N 29/036* (2013.01); *G01N 29/32* (2013.01); *H03B 5/1203* (2013.01); *H03B 5/326* (2013.01); *H03B 5/362* (2013.01); *H03H 9/02543* (2013.01); *H03H 9/02551* (2013.01); *H03H 9/02559* (2013.01);
(Continued)

(58) Field of Classification Search
CPC ..... B01L 2300/0663; B01L 2400/0436; G01N 29/036; G01N 29/32; H03B 5/30; H03B 5/32; H03B 5/326; H03B 5/36; H03B 5/362; H03B 5/364; H03B 5/366; H03B 5/368; H03B 2200/0022; H03B 2200/0038; H03H 9/02543; H03H 9/02551; H03H 9/02559; H03H 9/02637; H03H 9/02937; H03H 9/145; H03H 9/25
See application file for complete search history.

(56) References Cited

U.S. PATENT DOCUMENTS 3,836,873 A 9/1974 Healey, III et al.
3,878,481 A 4/1975 Healey, III
(Continued)

OTHER PUBLICATIONS

Kelly, R. D., "Electronic Circuit Analysis and Design by Driving-Point Impedance Techniques," IEEE Transactions on Education (1970) E-13(3):154-167.
(Continued)

*Primary Examiner* — Levi Gannon
(74) *Attorney, Agent, or Firm* — Madelynne J. Farber; Samantha Updegraff; Kenneth Paul McNiell

(57) ABSTRACT

The present invention relates to systems including an acoustic wave resonator and an active shunt capacitance cancelling oscillator circuit. Such systems can be used in biosensing methods, while avoiding impedance distortion and phase shift anomalies.

24 Claims, 17 Drawing Sheets

(51) Int. Cl.
*C12Q 1/18* (2006.01)
*G01N 29/036* (2006.01)
*G01N 29/32* (2006.01)
*H03B 5/12* (2006.01)
*H03B 5/32* (2006.01)
*H03H 9/02* (2006.01)
*H03H 9/145* (2006.01)
*H03H 9/25* (2006.01)

(52) U.S. Cl.
CPC .... *H03H 9/02637* (2013.01); *H03H 9/02937* (2013.01); *H03H 9/145* (2013.01); *H03H 9/25* (2013.01); *B01L 2300/0663* (2013.01); *B01L 2400/0436* (2013.01); *H03B 2200/0022* (2013.01); *H03B 2200/0038* (2013.01)

(56) References Cited

U.S. PATENT DOCUMENTS

| | | |
|---|---|---|
| 4,570,132 A | 2/1986 | Driscoll |
| 5,416,448 A | 5/1995 | Wessendorf |
| 6,169,459 B1 | 1/2001 | Wessendorf |
| 6,169,461 B1 | 1/2001 | Andoh et al. |
| 6,624,708 B1 | 9/2003 | Wessendorf |
| 7,804,374 B1 * | 9/2010 | Brown ............... H03B 5/36 331/96 |
| 7,878,063 B1 | 2/2011 | Cular et al. |
| 8,436,509 B1 | 5/2013 | Branch |
| 8,669,688 B1 | 3/2014 | Branch |
| 8,709,791 B2 | 4/2014 | Larson et al. |
| 9,512,421 B1 | 12/2016 | Branch et al. |
| 9,627,602 B1 | 4/2017 | Guzik |
| 10,031,135 B2 | 7/2018 | Larson et al. |
| 10,261,078 B2 | 4/2019 | Branch et al. |
| 2006/0055480 A1 | 3/2006 | Darrer et al. |
| 2006/0114072 A1 | 6/2006 | Lee et al. |
| 2010/0308930 A1 * | 12/2010 | Ayazi ............... H03B 5/368 331/154 |
| 2017/0052174 A1 * | 2/2017 | Branch ............. B01L 3/502715 |

OTHER PUBLICATIONS

Martin, S. J. et al., "Sensing Liquid Properties with Thickness-Shear Mode Resonators," Sandia National Laboratories, Albuquerque, New Mexico, Dec. 29, 1993, SAND94-0079J, 36 pages.

Wessendorf, K. O., "Quartz Oscillator Analysis," Sandia National Laboratories, Albuquerque, New Mexico, Jan. 1988, SAND87-0311, 31 pages.

* cited by examiner

ACOUSTIC WAVE RESONATOR WITH ACTIVE SHUNT CAPACITANCE CANCELLATION AND SYSTEMS THEREOF

RELATED APPLICATIONS

This application claims priority to U.S. Provisional Patent Application No. 62/932,297, filed on Nov. 7, 2019, entitled "ACOUSTIC WAVE RESONATOR WITH ACTIVE SHUNT CAPACITANCE CANCELLATION AND SYSTEMS THEREOF", the entirety of which is incorporated herein by reference for all purposes.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to systems including an acoustic wave resonator and an active shunt capacitance cancelling oscillator circuit. Such systems can be used in biosensing methods, while avoiding impedance distortion and phase shift anomalies.

BACKGROUND OF THE INVENTION

Acoustic wave systems can be used to detect mechanical and electrical changes in a sensitive manner. Such systems generally rely on extraction of certain parameters, e.g., changes in resonant frequency and/or amplitude, in order to ascertain the extent of such changes. Precise tracking of such parameters can be challenging, especially in light of non-zero electrical contributions that can arise from the system itself (e.g., contributions from resonator shunt capacitance). Thus, there is a need for advanced methods that avoid complicated signal deconvolution schemes to extract experimentally observed parameters.

SUMMARY OF THE INVENTION

The present invention relates, in part, to use of an active shunt capacitance cancelling oscillator circuit in conjunction with an active resonator. The circuit employs an equal "dummy" capacitance provided by an inactive resonator that possesses similar electrical properties as an active resonator. In addition, the circuit can also provide an output signal that is proportional to the amplitude of oscillation, which is also proportional to resonator loss. Such systems including the oscillator circuit, active resonator, and inactive resonator can provide more accurate tracking of resonator parameters, such as resonant frequency, and monitoring of only the acoustic contributions to be measured.

Accordingly, in a first aspect, the present invention features a system (e.g., sensor) including: an active resonator including a first piezoelectric substrate having a top surface; an electrode region disposed on the top surface of the first piezoelectric substrate, where the electrode region is configured to launch a shear horizontal surface acoustic wave and to detect the acoustic wave transmitted through the substrate; an inactive resonator including a second piezoelectric substrate; and an active shunt capacitance cancelling oscillator circuit. In some embodiments, the active shunt capacitance cancelling oscillator circuit includes an amplifier having an amplifier input and an amplifier output; a first transistor connected between the active resonator and the amplifier output; and a current mirror connected between the first transistor and the amplifier input. In particular embodiments, the current mirror is configured to provide a current component controlled by a capacitance of the inactive resonator, thereby effectively cancelling out a shunt capacitance associated with the active resonator.

In some embodiments, the system further includes one or more reflector regions disposed on the top surface of the first piezoelectric substrate and/or outside of a periphery of the electrode region. In particular embodiments, one or more reflector regions are configured to provide an acoustic cavity disposed within the first piezoelectric substrate, where the acoustic cavity is configured to store mechanical energy from the acoustic wave.

In some embodiments, a functionalized active area is disposed in proximity to the acoustic cavity. In other embodiments, the functionalized active area includes a plurality of cells (e.g., bacteria or bacterial cells, including immobilized cells). In other embodiments, the functionalized active area includes a plurality of capture agents (e.g., cells, proteins, etc.) configured to bind to or interact with one or more targets (e.g., drugs, analytes, antibiotics, antimicrobials, etc.).

In some embodiments, the system further includes an optional guide layer overlying the top surface of the first piezoelectric substrate, the electrode region, and the one or more reflector regions, or portions thereof. In other embodiments, a shear velocity in the guide layer is less than a shear velocity in the first piezoelectric substrate.

In some embodiments, the system further includes a fluidics module configured to be in fluidic communication with the functionalized active layer. In some embodiments, the fluidics module includes a fluidic layer having a sample chamber in fluidic communication with a surface (or a portion thereof) of the active resonator.

In some embodiments, the inactive resonator further includes an electrode region disposed on the top surface of the second piezoelectric substrate. In other embodiments, the electrode region of the inactive resonator is configured to minimize launching of a shear horizontal surface acoustic wave through the substrate. In yet other embodiments, the electrode region of the inactive resonator is configured to propagate an out-of-band or weakly coupled acoustic mode through the substrate, as compared to an acoustic mode including the shear horizontal surface acoustic wave through the substrate.

In a second aspect, the present invention features a system including: an active resonator including a first piezoelectric substrate; an inactive resonator including a second piezoelectric substrate; an amplifier including an amplifier input and an amplifier output; a first transistor connected between the active resonator and the amplifier output; and a first current mirror connected between the first transistor and the amplifier input. In some embodiments, the first current mirror is configured to provide a current component controlled by a capacitance of the inactive resonator, thereby effectively cancelling out a shunt capacitance associated with the active resonator. In some embodiments, the amplifier is a limiting amplifier.

In some embodiments, each of the active resonator and the inactive resonator includes an electrode region and one or more reflector regions disposed on the top surface of the piezoelectric substrate. In other embodiments, the one or more reflector regions of the active resonator are configured to provide an acoustic cavity disposed within the first piezoelectric substrate, where the acoustic cavity is configured to store mechanical energy from the acoustic wave.

In some embodiments, the active resonator further includes a functionalized active area disposed in proximity to the acoustic cavity of the active resonator. In some embodiments, the functionalized active area includes a plurality of immobilized cells. In other embodiments, the functionalized active area includes a plurality of capture agents configured to bind to or interact with one or more targets.

In some embodiments, the system further includes a tank circuit connected between ground and the amplifier input, where the tank circuit includes an inductor, a capacitor, and a resistor. In other embodiments, the system further includes a second transistor connected between the inactive resonator and the amplifier output; and a second current mirror connected between the first transistor and the second transistor.

In a third aspect, the present invention features a system including: an active resonator including a first piezoelectric substrate; an inactive resonator including a second piezoelectric substrate; an amplifier including an amplifier input and an amplifier output; a first transistor having an input connected to the amplifier output and a non-inverting output connected to the active resonator; a first current mirror connected between an inverting output of the first transistor and the amplifier input; a second transistor having an input connected to the amplifier output and a non-inverting output connected to the inactive resonator; and a second current mirror connected between an inverting output of the second transistor and the inverting output of the first transistor. In some embodiments, the first current mirror and/or the second current mirror are configured to provide a current component controlled by a capacitance of the inactive resonator, thereby effectively cancelling out a shunt capacitance associated with the active resonator.

In some embodiments, the one or more reflector regions of the active resonator are configured to provide an acoustic cavity disposed within the first piezoelectric substrate, where the acoustic cavity is configured to store mechanical energy from the acoustic wave. In other embodiments, the active resonator further includes a functionalized active area disposed in proximity to the acoustic cavity of the active resonator.

In a fourth aspect, the present invention features a method of detecting antimicrobial susceptibility of cells, the method including: delivering a compound to a plurality of immobilized bacterial cells in a functionalized active area disposed in proximity to an acoustic cavity; and measuring an output signal of the active resonator, where the output signal is provided by an active shunt capacitance cancelling oscillator circuit that effectively cancels out a shunt capacitance associated with the active resonator. In some embodiments, the acoustic cavity disposed within an active resonator is configured to store mechanical energy from an acoustic wave.

In some embodiments, the output signal indicates growth or inhibition of the plurality of immobilized bacterial cells. In other embodiments, the output signal includes a series resonance frequency, a frequency shift, or an amplitude change.

In some embodiments, the active shunt capacitance cancelling oscillator circuit includes any components described herein. In other embodiments, the oscillator circuit includes an amplifier including an amplifier input and an amplifier output; a first transistor connected between the active resonator and the amplifier output; and a current mirror connected between the first transistor and the amplifier input, where the current mirror is configured to provide a current component controlled by a capacitance of an inactive resonator, thereby effectively cancelling out the shunt capacitance associated with the active resonator.

In some embodiments, the delivering step further includes delivering the compound to a fluidics module in fluidic communication with the functionalized active area.

In any embodiment herein, each of the first piezoelectric substrate and the second piezoelectric substrate includes the same material (e.g., any herein). In some embodiments, the first and/or second piezoelectric substrate includes lithium tantalate, lithium niobate, potassium niobate, or quartz.

In any embodiment herein, the active resonator and/or the inactive resonator includes an electrode region disposed on the top surface of the piezoelectric substrate. In some embodiments, the active resonator and/or the inactive resonator includes one or more reflector regions disposed on the top surface of the piezoelectric substrate. In particular embodiments, the one or more reflector regions of the active resonator are configured to provide an acoustic cavity disposed within the first piezoelectric substrate, where the acoustic cavity is configured to store mechanical energy from the acoustic wave. In other embodiments, the active resonator and/or the inactive resonator further includes a functionalized active area disposed in proximity to the acoustic cavity.

In any embodiment herein, the active resonator and the inactive resonator includes an identical electrode design. In some embodiments, the identical electrode design is positioned along a first crystal axis of the first piezoelectric substrate and a second crystal axis of the second piezoelectric substrate, in which the first and second crystal axes are different.

In any embodiment herein, the first piezoelectric substrate is configured to propagate the shear horizontal surface acoustic wave, and the second piezoelectric substrate is configured to propagate an out-of-band or weakly coupled acoustic mode, as compared to an acoustic mode including the shear horizontal surface acoustic wave.

In any embodiment herein, a functionalized active area is disposed in proximity to the acoustic cavity. In some embodiments, the functionalized active area includes a plurality of cells (e.g., bacteria or bacterial cells). In other embodiments, the plurality of cells includes a plurality of immobilized cells (e.g., a plurality of immobilized bacteria). In yet other embodiments, the functionalized active area includes a plurality of capture agents (e.g., cells, proteins, etc.) configured to bind to or interact with one or more targets (e.g., drugs, analytes, antibiotics, antimicrobials, etc.).

In any embodiment herein, the system further includes a tank circuit connected between ground and the amplifier input, where the tank circuit includes an inductor, a capacitor, and a resistor.

In any embodiment herein, a connection between two circuit components include direct or indirect electrical connections. For instance, any such connection herein (e.g., in parallel) can include one or more capacitors to facilitate an ac connection or one or more current sources for biasing (e.g., dc biasing).

Definitions

As used herein, the term "about" means+/−10% of any recited value. As used herein, this term modifies any recited value, range of values, or endpoints of one or more ranges.

By "disposed" is meant that a first structure is located in a particular position relative to a second structure. This position includes direct contact between the first and second structures (e.g., direct continuous or noncontinuous contact) or indirect contact between the first and second structures (e.g., by way of third or further structure(s) disposed between the first and second structures).

By "electrical connection," as used herein, refers to any conductive or semi-conductive structure through which an electrical signal may pass. The electrical signal can be any useful change in electrical field, electric potential, current, or voltage. Non-limiting structures include lines, contact pads, busses, pins, connectors, bond lines, bond pads, etc., formed from any useful material (e.g., an ohmic material, a metal, etc.).

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

By "microfluidic" or "micro" is meant having at least one dimension that is less than 1 mm and, optionally, equal to or larger than about 1 μm. For instance, a microfluidic structure (e.g., any structure described herein) can have a length, width, height, cross-sectional dimension, circumference, radius (e.g., external or internal radius), or diameter that is less than 1 mm.

By "nano" is meant having at least one dimension that is less than 1 μm but equal to or larger than about 1 nm. For instance, a nanostructure (e.g., any structure described herein, such as a nanoparticle) can have a length, width, height, cross-sectional dimension, circumference, radius (e.g., external or internal radius), or diameter that is less than 1 μm but equal to or larger than about 1 nm. In other instances, the nanostructure has a dimension that is of from about 1 nm to about 1 μm.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

DETAILED DESCRIPTION OF THE INVENTION

Figure 1A:
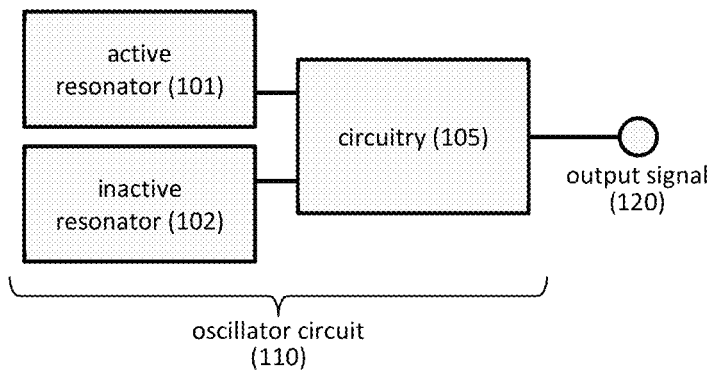
FIGS. 1A-1C show components of an exemplary system. Provided are (A) an exemplary system including an active resonator 101, an inactive resonator 102, and a circuitry 105 configured to provide an output signal 120 that compensates for non-zero shunt capacitance of the active sensor; (B) an exemplary oscillator circuit; and (C) an exemplary system including resonator(s) 130, a fluidics module 140, and a printed circuit board 150.

The present invention relates to systems that can be used as an acoustic wave sensor. The system also includes circuitry that allows non-zero shunt capacitance of the active sensor to be removed by using an inactive sensor as a dummy capacitance. FIG. 1A provides an exemplary system including an active resonator 101 and an inactive resonator 102, as well as circuitry 105 connected to both the active and inactive resonators 101,102. In this way, the circuitry provides a circuit that employs the capacitance of the inactive resonator 102 to cancel out a shunt capacitance associated with the active resonator 101. The circuitry can employ any useful components (e.g., described herein, such as one or more amplifiers, transistors, current mirrors, tank circuits, etc.) configured to provide an output signal 120 that compensates for the non-zero shunt capacitance of the active sensor 101. Such compensation can employ an inactive sensor, which possesses all the electrical characteristics of the active sensor but lacks the ability to effectively propagate an acoustic wave.

In one non-limiting instance, the active and inactive sensor can be formed from the same piezoelectric material, as well as possess the same electrode design, reflector region, optional guide layer, etc. However, the active sensor can be electrically connected to launch a shear horizontal surface acoustic wave along a crystal orientation that sufficiently propagates that wave, whereas the inactive sensor can be electrically connected along a crystal orientation that does not sufficiently propagate a shear horizontal surface acoustic wave. For example, if the piezoelectric material is ST-quartz, the shear-horizontal leaky surface acoustic wave (SH-LSAW) mode propagates along the 90° rotation to the axis (ST-90° X), and a weak Rayleigh mode propagates along the X-axis (ST-X), in which these two acoustic modes are separated in frequency by a factor of about 1.5 times. Thus, an active sensor can include a ST-quartz substrate configured to propagate a SH-LSAW along the 90° rotation to the X-axis, and the inactive sensor can include a ST-quartz substrate configured to propagate a Rayleigh wave along the X-axis.

Any other useful configuration or type of piezoelectric substrates can be employed, with the general requirement that an acoustic mode of the active sensor can be distinguished or separated from the acoustic mode of the inactive sensor. For instance, different materials will possess different waves along different crystal orientations. Thus, in one embodiment, an active sensor can include a piezoelectric material cut a first crystal orientation, and an inactive sensor can include that same piezoelectric material cut at a second crystal orientation that is different than the first crystal orientation. In another embodiment, the crystal cut and material are the same for the active and inactive sensors, but the electrode regions are deposited along different axes of the crystal orientation, thereby providing differing directions of wave propagation along different crystal axes.

Figure 1B:
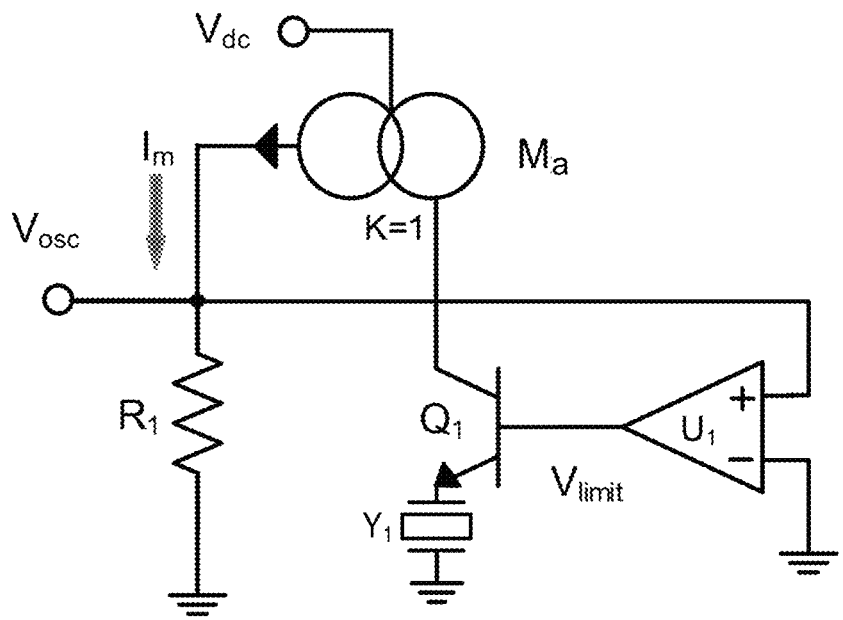

By minimizing acoustic propagation within the inactive sensor, a matched capacitor is formed. Such a capacitor can be employed as a reference capacitor within an oscillator circuit to remove non-zero shunt capacitance of the active sensor. FIG. 1B provides an exemplary oscillator circuit including an active resonator $Y_1$; an amplifier $U_1$ including an amplifier input and an amplifier output; a first transistor $Q_1$ connected between the active resonator and the amplifier output; and a current mirror $M_a$ connected between the first transistor and the amplifier input, wherein the current mirror is configured to provide a current component $I_m$ controlled by a capacitance of an inactive resonator, thereby effectively cancelling out a shunt capacitance associated with the active resonator. Contribution of the inactive resonator can be provided to the current mirror $M_a$ in any useful manner. In one non-limiting embodiment, another current mirror $M_b$ passes a copy of the capacitance from the inactive resonator to current mirror $M_a$. Additional schematics for circuits and components thereof are described herein.

Figure 1C:
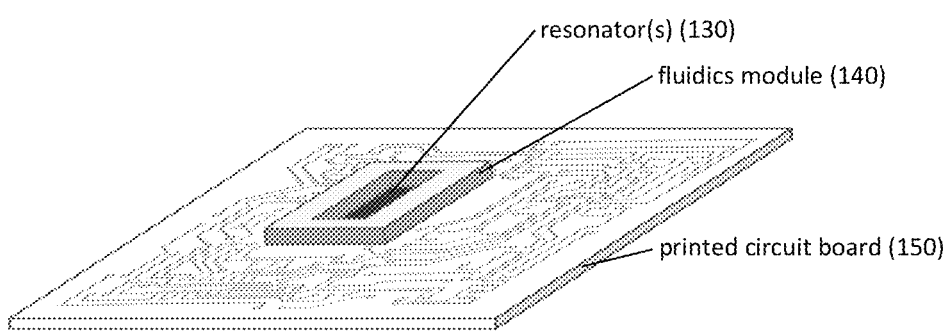

The system can include any useful modules to facilitate assembly of the sensors and its use. For example, as seen in FIG. 1C, the system can include a fluidics module 140 to deliver a fluid (e.g., a sample, a compound, a buffer, etc.) to a functionalized area of the resonator 130. In one embodiment, the fluidics module can include a sample chamber configured to be in fluidic communication with the functionalized active area. The system can also include any useful electronics module configured to provide an electrical connection to the resonator(s) 130 and to provide an oscillator circuit, such as, e.g., by use of a printed circuit board 150 having one or more electrical contacts configured to provide one or more electrical connections to the resonator(s). Additional modules are described herein.

Active Shunt Capacitance Cancelling Oscillator Circuits

Typically, an oscillator circuit is employed to track series resonance frequency $F_s$ of a resonator, as a network analyzer requires additional post-processing to locate $F_s$. Yet, use of oscillator circuits can still remain a challenge, as non-zero shunt capacitance of the active resonator can impact accurate reporting of the effects of an environmental change on $F_s$. In particular, if shunt capacitance $C_o$ can be removed, then $F_s$ would occur exactly where the phase crosses zero. The present invention relates, in part, to use of an oscillator circuit that employs an inactive resonator for active shunt capacitance cancelling. In particular embodiments, the inactive resonator has the same electrical and acoustic characteristics of an active resonator, but the inactive resonator propagates an acoustic mode (e.g., a Rayleigh mode) that is not acoustically active, thus serving as a reference capacitor.

Figure 5:
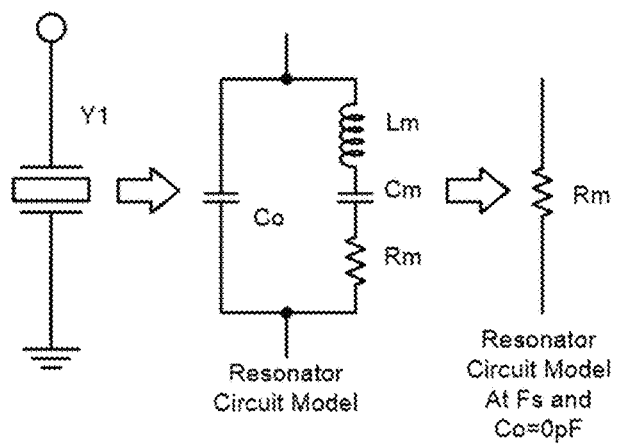
FIG. 5 shows an equivalent circuit of a 1-port acoustic resonator.

FIG. 5 shows a simplified circuit model of a single port resonator $Y_1$, which can be represented by a circuit model that includes a motional arm containing an inductance $L_m$, a capacitance $C_m$, and a resistance $R_m$. This motional arm of the resonator represents the piezoelectric characteristics of the resonator, and shunt capacitance $C_o$ is a parasitic capacitance arising from external to the piezoelectric crystal (e.g., due to the plating of the electrodes on the resonator substrate). The series resonance frequency $F_s$ is defined as the frequency in which $L_m$ and $C_m$ are in resonance, thus providing a measure of resonator loss $R_m$ when $C_o$ is 0 or $C_o$ is a very large reactance, as compared to $R_m$.

With $C_o$ removed, one can use a series resonant oscillator circuit that monitors the zero impedance phase point of this motional arm, which occurs at $F_s$ of the resonator (FIGS.

6A-6B). Also, one can extract the value of $R_m$ from a series resonant oscillator that removes shunt capacitance, as the resonator impedance is simply $R_m$ at $F_s$ without requiring signal deconvolution. Thus, by minimizing $C_o$, determining relevant parameters (e.g., $F_s$ and/or $R_m$) become simplified.

Yet, $C_o$ is typically a non-zero value due to external contributions, in which interactions between the piezoelectric substrate with electrode plating or fixtures can affect acoustic contributions to $F_s$ and/or $R_m$. Herein, shunt capacitance across the resonator is removed by supplying the circuit an equal "dummy" capacitance, which is used to generate a cancelling current used in the oscillator to electronically cancel the non-desired resonator shunt capacitance. This circuit also supplies an output signal (e.g., a dc voltage) that is proportional to the amplitude of oscillation, which is also proportional to $R_m$.

Figure 7A:
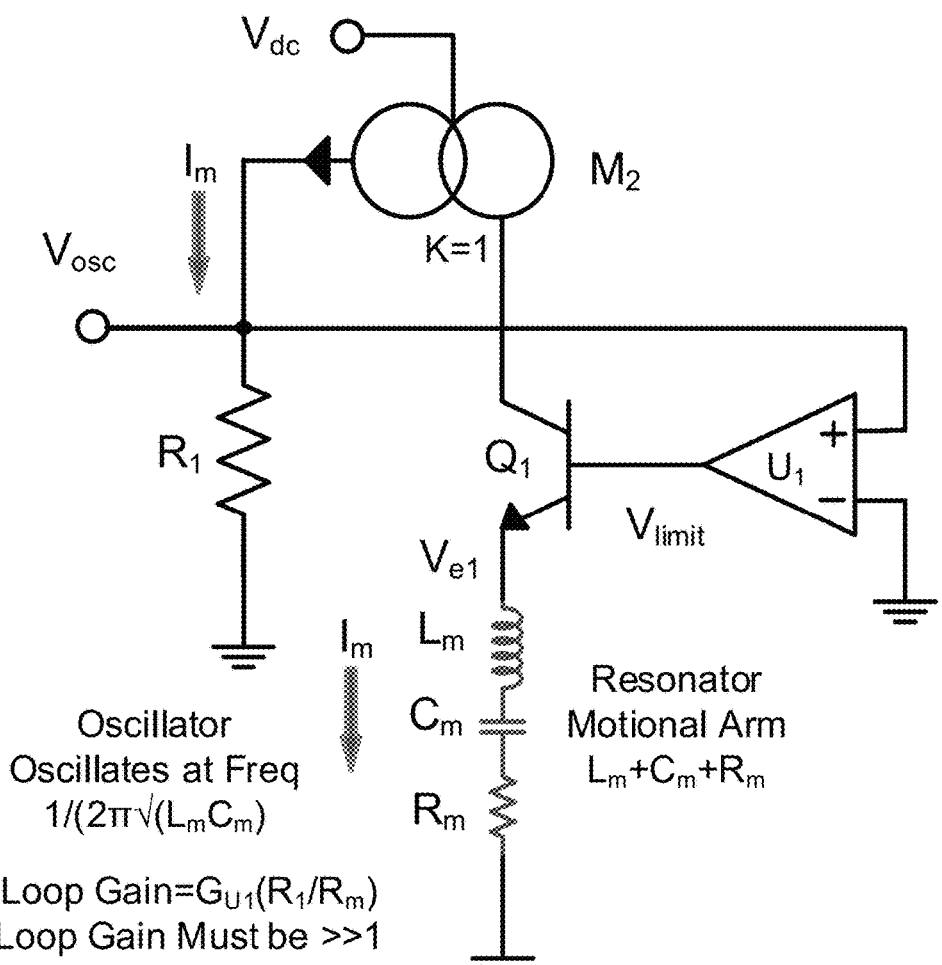
FIGS. 7A-7B show exemplary oscillator circuits with active shunt $C_o$ removal. Provided are (A) an exemplary circuit including a single current mirror $M_2$ and (B) another exemplary circuit including two current mirrors $M_1$, $M_2$.

FIG. 7A provides an exemplary simplified oscillator circuit for a single port resonator. The active resonator is represented by a motional arm containing $L_m$, $C_m$, and $R_m$. Ideally, current $I_m$ is passed from the current mirror $M_2$ to the motional arm in a manner that shunt capacitance is cancelled, leaving only the motional arm current. Herein, current $I_m$ is controlled by a capacitance of the inactive resonator, thereby effectively cancelling out a shunt capacitance associated with the active resonator.

Figure 7B:
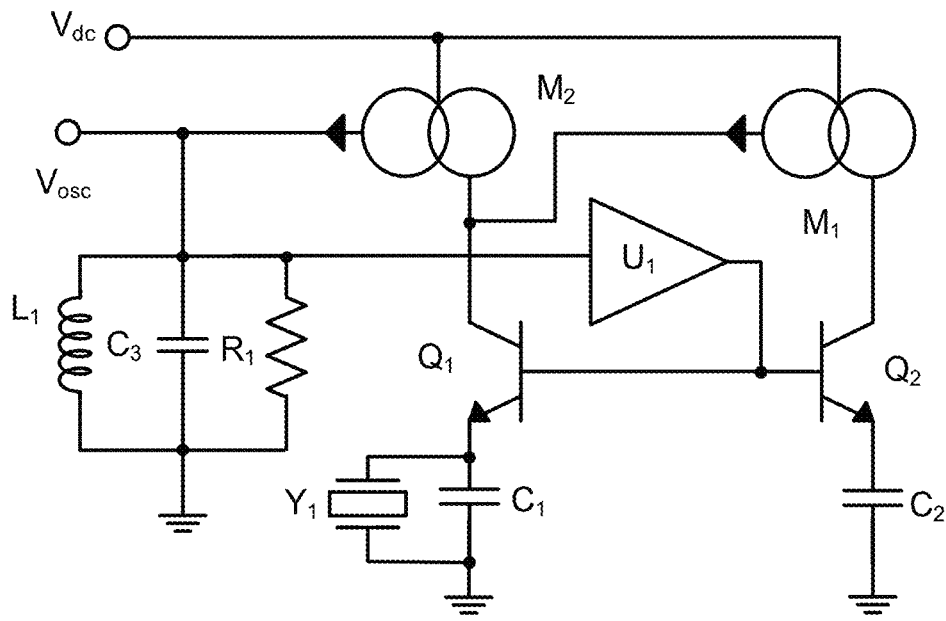

FIG. 7B provides a functional diagram of an exemplary oscillator circuit, which employs a dummy capacitor $C_2$ (e.g., an inactive resonator) to electronically remove the total shunt capacitance of the resonator $Y_1$ at emitter $Q_1$. Such a design could allow for accurate fs and resonator loss determination and can be implemented in any useful manner (e.g., as any electronics module described herein, such as a PCB with electrical connections). As can be seen, the circuit includes an active resonator $Y_1$ with shunt capacitance $C_1$, an inactive resonator $C_2$, an amplifier $U_1$, a first transistor $Q_1$ (having an input connected to the amplifier output and a non-inverting output connected to the active resonator), a first current mirror $M_2$ (connected between an inverting output of the first transistor and the amplifier input), a second transistor $Q_2$ (having an input connected to the amplifier output and a non-inverting output connected to the inactive resonator), and a second current mirror $M_1$ (connected between an inverting output of the second transistor and the inverting output of the first transistor). In this configuration, current mirrors $M_1$, $M_2$ provide a current component controlled by a capacitance of the inactive resonator $C_2$, thereby effectively cancelling out a shunt capacitance $C_1$ associated with the active resonator $Y_1$. Optionally, the circuit can include a tank circuit having an inductance $L_1$, a capacitance $C_3$, and a resistance $R_1$.

In use (FIG. 8A), the oscillator circuit employs the emitters of $Q_1$ and $Q_2$ as active ports to convert impedances of the active resonator $Y_1$ with shunt capacitance $C_1$ and a dummy capacitance $C_2$ into currents that will be summed at an output node. In this way, the equivalent circuit functions as an oscillator, where the frequency of oscillation only depends on the motional arm of the resonator circuit. To cancel the effects of the shunt capacitance across the resonator $C_o+C_1$, the value of $C_2$ needs to equal $C_o+C_1$. In addition, current mirror $M_1$ passes on a copy of the dummy capacitance current $I_{C2}$ to mirror $M_2$, where the summing of the two current legs across $Q_1$ and $Q_2$ cancels the shunt capacitance currents and leaves only the motional arm current $I_m$ to provide an output voltage $V_{osc}$ at node $R_1$.

The gain of amplifier $U_1$ is real, in which loop gain $A_v$ is $R_1(G_{U1})/(X_{Lm}+X_{Cm}+R_m)$, where $X_{Lm}$ and $X_{Cm}$ are the reactance of $L_m$ and $C_m$, respectively. The oscillator will oscillate when $A_v$ is greater than one, and the oscillation frequency is determined by where this loop function is real (or 360 degrees), which only occurs when $X_{Cm}+X_{Lm}=0$ or when $F_{osc}=1/(2\pi\sqrt{(L_mC_m)})$. The loop gain equation at this frequency is $R_1(G_{U1})/R_m$. The voltage at node $V_{osc}$ is then simply the limiting voltage of $U_1$ multiplied by the ratio of $R_1/R_m$.

In some embodiments, at the node $V_{osc}$, $R_1$ can employ a parallel tank circuit to provide a wider range of operational frequencies and/or selection of a resonator overtone, if desired. FIG. 8B provides a simplified active shunt canceling oscillator with a tank circuit. The output tank, at $V_{osc}$, is a relatively low Q parallel tank circuit, where $L_1$ is chosen to be resonant with $C_3$ at the desired resonator frequency.

Figure 9:
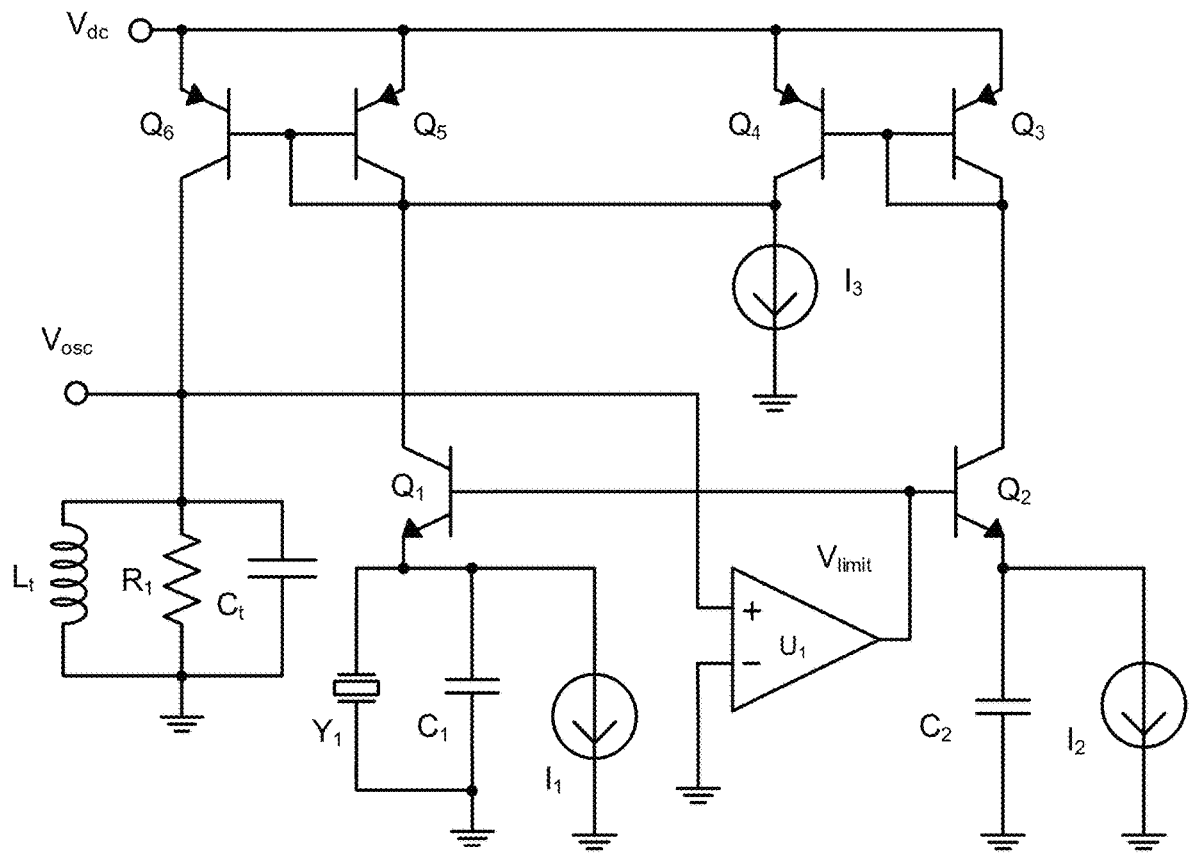
FIG. 9 shows yet another exemplary oscillator circuit with active shunt $C_o$ removal.

FIG. 9 shows an implementation of an oscillator circuit. As can be seen, the circuit includes an active resonator $Y_1$ with shunt capacitance $C_1$, a first current source $I_1$ connected in parallel to the active resonator, an inactive resonator $C_2$, a second current source 12 connected in parallel to the inactive resonator, an amplifier $U_1$, a first transistor $Q_1$ (having an input connected to the amplifier output and a non-inverting output connected to the active resonator), a first current mirror (formed from a fifth transistor $Q_5$ and a sixth transistor $Q_6$, which is connected between an inverting output of the first transistor and the amplifier input), a second transistor $Q_2$ (having an input connected to the amplifier output and a non-inverting output connected to the inactive resonator), a second current mirror (formed from a third transistor $Q_3$ and a fourth transistor $Q_4$, which is connected between an inverting output of the second transistor and the inverting output of the first transistor), and a third current source $I_3$ connected between first and second current mirrors. Optionally, the circuit can include a tank circuit having an inductance $L_t$, a capacitance $C_t$, and a resistance $R_1$ at a node.

One or more components can be included in the oscillator circuit. For instance, an amplifier (e.g., a limiting amplifier) can be employed in a feedback loop about a first transistor, with a non-inverting output of the first transistor being connected to drive the resonator at the frequency of oscillation. The limiting amplifier can be, e.g., a differential amplifier with one input connected to an inverting output of a transistor and with another input being electrically grounded at the frequency of oscillation. The output of the limiting amplifier can be connected to the input of the transistor to provide positive feedback for oscillation. The limiting amplifier can optionally provide a frequency output signal that is representative of the frequency of oscillation of the resonator, and a dc voltage output signal that is representative of a resonator loss component $R_m$. In another embodiment, the limiting amplifier comprises a differential amplifier with a first amplifier input being capacitively coupled to the inverting output of the transistor and with a second amplifier input being capacitively coupled to an electrical ground.

A plurality of transistors can be provided in any useful configuration. In one embodiment, a second transistor has its input connected to the input of a first transistor and further connected to the output of a limiting amplifier, which is located in a feedback loop between the inverting output of the first transistor and the inputs of both transistors to provide the positive feedback necessary for oscillation of the resonator(s).

A resonant tank circuit can be employed, e.g., a low-Q tank circuit that is used to connect the oscillator circuit to a power supply. In one instance, the inverting output of the first transistor can be connected to a resonant tank circuit to suppress oscillation of the resonator at frequencies other than near the series resonance. This resonant tank can be configured to peak the gain of the tuned gain stage in a desired frequency range near the series resonance frequency $F_s$ and helps to reject unwanted modes of oscillation. The circuit can further include a current source provided between the non-inverting transistor output and an electrical ground for direct-current (dc) biasing of the transistor.

The oscillator circuit can employ one or more current mirrors for providing current components. In one embodiment, the current mirror provides dc and/or alternating-current (ac) current components at the non-inverting output of a transistor (e.g., a first transistor having a non-inverting output connected to an active resonator), with the ac current component being equal in magnitude and phase to a current flow through the shunt capacitance associated with the active resonator at the frequency of oscillation. This ac current component effectively cancels out any shunt of the active resonator due to the shunt capacitance by providing all the current flow through the shunt capacitance. The value of this ac current component is determined by an inactive resonator (e.g., as described herein). Those skilled in the art will understand that there are many different ways of forming current mirrors depending on the particular type of circuit elements used (e.g., NPN or PNP bipolar transistors, field-effect transistors, or cascode devices) and other considerations (e.g., temperature compensation).

Current sources are preferably provided within the oscillator circuit at the non-inverting outputs of each transistor (e.g., in parallel with the active resonator and/or in parallel with the inactive resonator) to establish dc bias levels for these transistors. The functional elements of the oscillator circuit (e.g. the first and second transistors, the limiting amplifier, and the current mirror) can be optionally formed as an integrated circuit (IC).

Those skilled in the art will understand that other circuit designs can be formed based on the teachings of the present invention for operating at the same or different frequencies, and for operating at the same or a different supply voltage. Furthermore, those skilled in the art will understand that the oscillator circuit of the present invention can be formed with other types of transistors, including field effect transistors. Those skilled in the art will also understand that all or part of the oscillator circuit of the present invention can be formed as a discrete circuit, as a hybrid circuit or as an IC.

Embodiments of the oscillator circuit of the present invention can be formed using either bipolar transistors or field-effect transistors (FETs). When the oscillator circuit is formed as an IC, certain components (e.g., tank circuit) can be outboard of the IC to allow adaptation of the IC to many different types of applications, or to different types and sizes of piezoelectric crystals.

Resonators

A resonator (e.g., an active resonator) can include an acoustic cavity configured to store mechanical energy from the acoustic wave. In some embodiments, the cavity is formed by employing one or more reflector regions (e.g., by use of reflectors, such as Bragg gratings). The cavity stores the mechanical energy from the multi-pass wave. Because acoustic standing waves of the resonator can reflect back and forth a plurality of times (e.g., about 100 times or more) through the cavity in the process of achieving resonance, the resonator has enhanced sensitivity (e.g., a greater sensitivity than a sensor employing a SH-SAW delay-line that lacks the acoustic cavity).

The area of the cavity can be minimized, as needed, which in turn minimizes sample use. In some embodiments, the area can be from about 0.01 $mm^2$ to about 10 $mm^2$, such as from 0.01 $mm^2$ to 5 $mm^2$, 0.01 $mm^2$ to 1 $mm^2$, 0.01 $mm^2$ to 0.5 $mm^2$, 0.01 $mm^2$ to 0.1 $mm^2$, 0.05 $mm^2$ to 10 $mm^2$, 0.05 $mm^2$ to 5 $mm^2$, 0.05 $mm^2$ to 1 $mm^2$, 0.05 $mm^2$ to 0.5 $mm^2$, 0.05 $mm^2$ to 0.1 $mm^2$, 0.1 $mm^2$ to 10 $mm^2$, 0.1 $mm^2$ to 5 $mm^2$, 0.1 $mm^2$ to 1 $mm^2$, 0.1 $mm^2$ to 0.5 $mm^2$, 0.5 $mm^2$ to 10 $mm^2$, 0.5 $mm^2$ to 5 $mm^2$, 0.5 $mm^2$ to 1 $mm^2$, 1 $mm^2$ to 10 $mm^2$, or 1 $mm^2$ to 5 $mm^2$. In some embodiments, a sample volume can be reduced to less than about 50 nL, such as from about 0.5 nL to 5 nL, 0.5 nL to 10 nL, 0.5 nL to 25 nL, 0.5 nL to 50 nL, 1 nL to 5 nL, 1 nL to 10 nL, 1 nL to 25 nL, 1 nL to 50 nL, 2 nL to 5 nL, 2 nL to 10 nL, 2 nL to 25 nL, 2 nL to 50 nL, 5 nL to 10 nL, 5 nL to 25 nL, 5 nL to 50 nL, 10 nL to 25 nL, or 10 nL to 50 nL.

The active area of a resonator can be disposed in proximity to the acoustic cavity. In this way, changes occurring in proximity to the active area can be detected by a change in an acoustic parameter, such as resonant frequency, amplitude, etc. In one instance, the active area can include immobilized cells, and changes to the cells can result in an environmental change (e.g., growth of cells within the active area, thereby providing an increase in mass; or inhibition of cells within the active area, thereby providing a decrease in mass) to the cavity. In turn, these environmental changes can either increase or decrease the velocity of the acoustic waves within the cavity, which translates to a resonant frequency shift that can be measured electrically.

In another instance, specificity for a particular target can be imparted by capture agents deposited within the active area. Binding of a target to the capture agent results in an environmental change (e.g., a mass change) to the cavity, where such binding decreases the velocity of the acoustic waves traveling within the acoustic cavity. This decrease in velocity then translates to a resonant frequency shift, which can be measured electrically.

An electrode region can include a transmitting transducer, which launches the acoustic wave by applying an electrical distribution field to a piezoelectric substrate; and the reflection region confines the wave within a cavity. In particular embodiments, the reflection region(s) are disposed outside of a periphery of the electrode region, thereby confining the wave and minimizing loss into the surrounding substrate. The electrode region can further include a receiving transducer, which detects the acoustic wave and transduced the mechanical wave into an electrical signal by inverse piezo-electrical coupling.

Figure 19A:
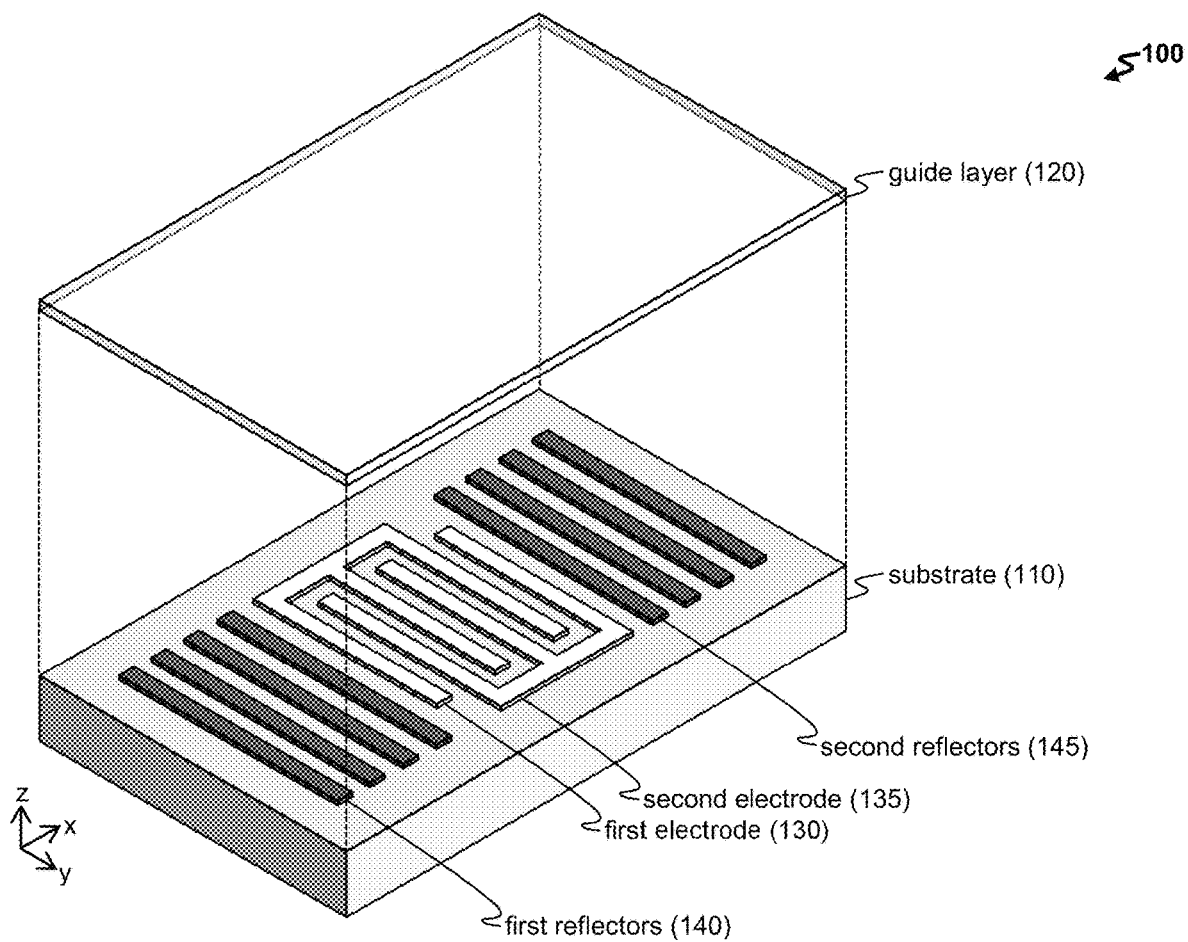
FIGS. 19A-19D show schematics of an exemplary resonator having various components. Provided are (A) an exemplary one-port resonator 100 in an exploded view, (B) an assembled resonator 1000, (C) a cross-sectional view along line 19C-19C in FIGS. 19B, and (D) a plan view of the top surface of the resonator.

FIG. 19A shows an exemplary resonator 100, which includes a piezoelectric substrate 110 and an electrode region configured to generate and detect acoustic waves. In one exemplary embodiment, the resonator is configured as a one-port device having a pair of transducers. Each pair includes a transmitting transducer and a receiving transducer, in which the transmitting transducer is an active electrode configured to provide an electrical field and the receiving transducer is a grounded electrode configured to transduce the acoustic wave back into an electrical signal.

Figure 19B:
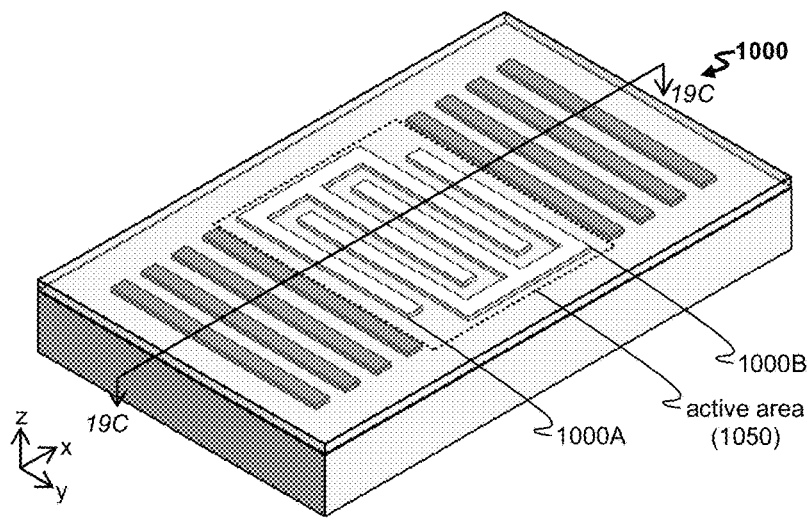

The electrode region can be characterized by a first edge and a second edge, in which the first and second edges are parallel to each other and are perpendicular to the propagation direction (i.e., the first direction). As seen in FIG. 19A, the electrode region includes a first electrode 130 and a second electrode 135. As seen in FIG. 19B, a first edge 1000A of the electrode region is defined to be along the y-axis and along an edge of the first finger in the first electrode 130; the second edge 1000B of the electrode region is also defined to be along the y-axis and along an edge of the last finger in the second electrode 135. When configured thusly, the propagation direction of the acoustic wave is along the x-axis.

Figure 20:
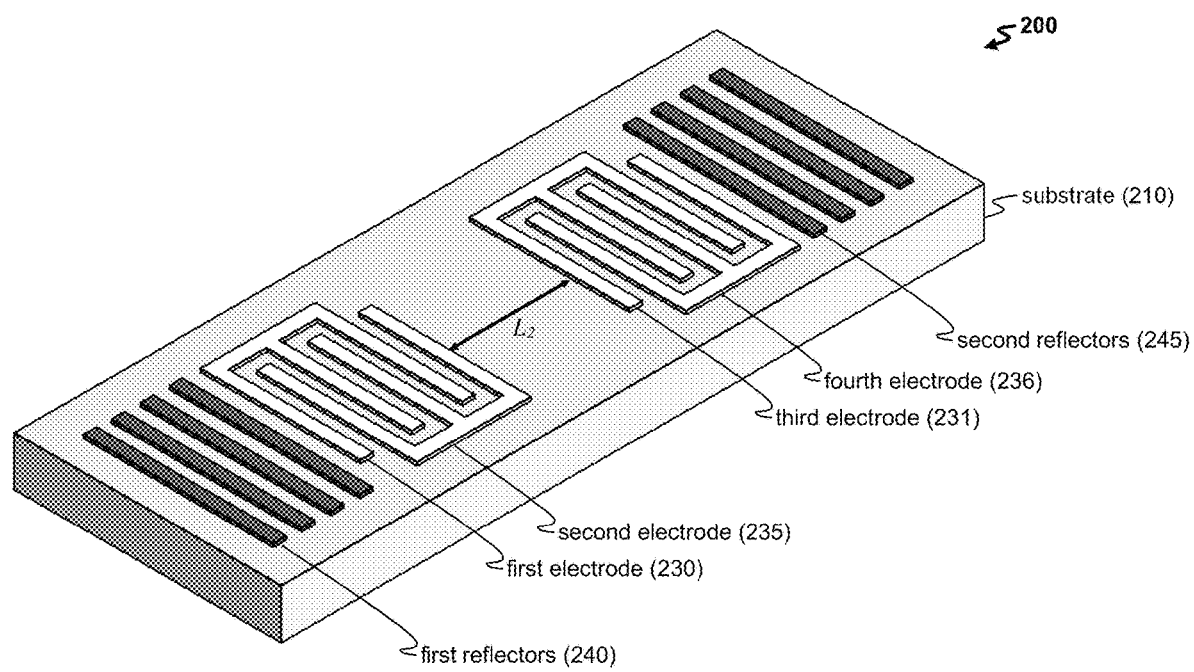
FIG. 20 shows a schematic of an exemplary two-port resonator 200 having a spacing $L_2$ between two transducer pairs.

Turning again to FIG. 19A, the first electrode 130 and the second electrode 135 can be interdigitated transducers (IDT), in which comb electrodes are arranged to interdigitate the fingers of the electrodes. One of these electrodes can be an active electrode, and the other a grounded electrode. Each electrode can have any useful configuration and geometry. Other useful configurations and geometries for the electrodes can be employed. For instance, FIG. 20 provides a resonator 200 having a two-port configuration, as described herein, in which two pairs of transducers are employed.

The resonator can further include one or more reflector regions disposed on a surface of the piezoelectric substrate. The reflector region(s) are arranged to provide an acoustic cavity that confines the acoustic wave within a region of the piezoelectric substrate. As seen in FIG. 19A, the resonator 100 can include a first reflector region having a plurality of first reflectors 140 and a second reflector region having a plurality of second reflectors 145. The reflector region can have any useful configuration and geometry (e.g., as described herein). The reflector region can include any type of reflector (e.g., a bar, a grating, an electrode, etc., in an optional array), which can be provided in a grounded configuration, an open configuration, and/or a closed configuration. For instance, a first reflector region can be located in proximity to a first edge 1000A of the electrode region; and the second reflector region can be located in proximity to a second edge 1000B of the electrode region. The distance between an edge of the first reflector region and the first edge of the electrode region can be any useful distance (e.g., as described herein).

In another instance, a major dimension of the reflector region can be configured to be parallel to the first edge of an electrode and perpendicular to the propagation direction (i.e., the first direction). As seen in FIG. 19B, the major dimension of the reflector region (e.g., a reflector length) is along they-axis, and this major dimension is parallel to the first edge 1000A and perpendicular to the propagation direction that is along the x-axis.

The resonator can include an optional guide layer in order to confine the surface acoustic wave to the surface, rather than allowing the wave to leak into the bulk substrate. When a guide layer is disposed on a surface of the piezoelectric substrate (e.g., in which the shear velocity in the guide layer is less than the shear velocity in the piezoelectric substrate), the surface wave is confined within the guide layer, and the confined wave is characterized as a Love wave. Based on the orientation of the piezoelectric substrate (e.g., a specific cut that is oriented along a particular crystal) and the orientation of the electrode region, particular types of acoustic waves can be generated. In one embodiment, the orientation is such that the surface acoustic wave (SAW) is a shear wave that is horizontally polarized (a shear horizontal wave or SH wave). The wave is shear because the particle displacement of the wave is perpendicular to the wave propagation direction. In addition, the wave is horizontally polarized because the particle displacement of the wave is parallel to a surface of the substrate.

FIG. 19A shows an optional guide layer 120 disposed above the substrate 110 and other components (e.g., including the first and second electrodes 130,135, as well as the first and second reflectors 140,145). To propagate a Love wave, the material and thickness of the guide layer can be optimized to provide a shear velocity that is lower than the shear velocity of the piezoelectric material. In another instance, the guide layer is selected to allow one or more capture agents to be bound to a surface of the guide layer (by way of indirect or direct binding). In an embodiment, the guide layer can be treated with one or more capture agents or cells, thereby providing a functionalized surface. When that surface overlies the acoustic cavity, then a functionalized active area is formed. As seen in FIG. 19B, the assembled resonator 1000 includes an active area 1050 located above the acoustic cavity bounded by the reflector regions, and this active area 1050 can be treated with one or more capture agents to form a functionalized active area.

Figure 19C:
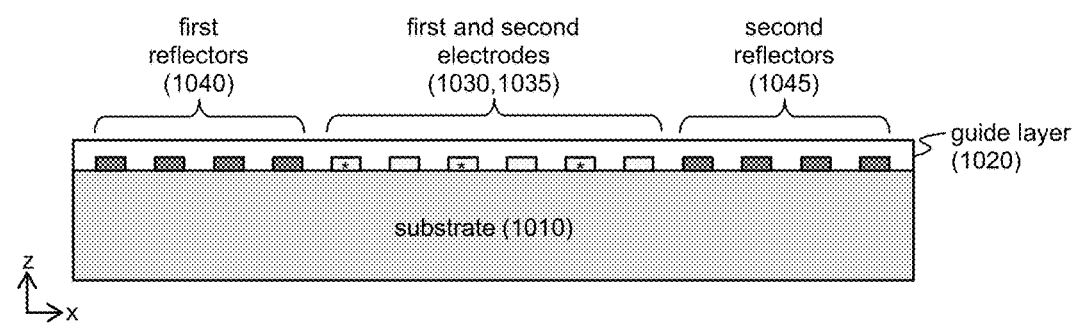

In yet another instance, an optional guide layer can be employed to electrically isolate the components of the resonator, e.g., to isolate the fingers of the first electrode from the fingers of the second electrode. In this case, the material can be chosen to be a dielectric material (e.g., an insulator, such as a silicon oxide or a silicon nitride), which is disposed as a layer having a sufficient thickness that overlies the electrode region. FIG. 19C provides an exemplary resonator in which the guide layer 1020 overlies a top surface of the substrate 1010, as well as the electrodes 1030,1035 of the electrode region and the first and second reflectors 1040,1045 of the reflector regions. In this configuration, the guide layer protects the components of the resonator from the liquid sample.

The positions and configuration of the electrode regions and reflector regions can be optimized. In one instance, the reflector region(s) can be arranged in any useful location with respect to the electrode region. For example, the electrode region can include one or more transducers, which in turn are arranged to provide an acoustic wave that propagates along a first direction. To effectively isolate and confine that wave, the reflection region can be arranged to interfere and reflect the acoustic wave a multiple of times within an active area. In one instance, the reflector region has a first reflective edge, and this edge is positioned to be perpendicular to the first direction (i.e., the propagation direction of the acoustic wave). Furthermore, to minimize destructive interference and maximize reflection, the reflector region can be positioned to be in proximity to an edge of the electrode region (e.g., separated by a distance d that is a fractional portion of the characteristics acoustic wavelength $\lambda$, such as $\pm 1/8\lambda$, $\pm 1/4\lambda$, $\pm 3/8\lambda$, $\pm 1/2\lambda$, $\pm 3/4\lambda$, etc.).

Figure 19D:
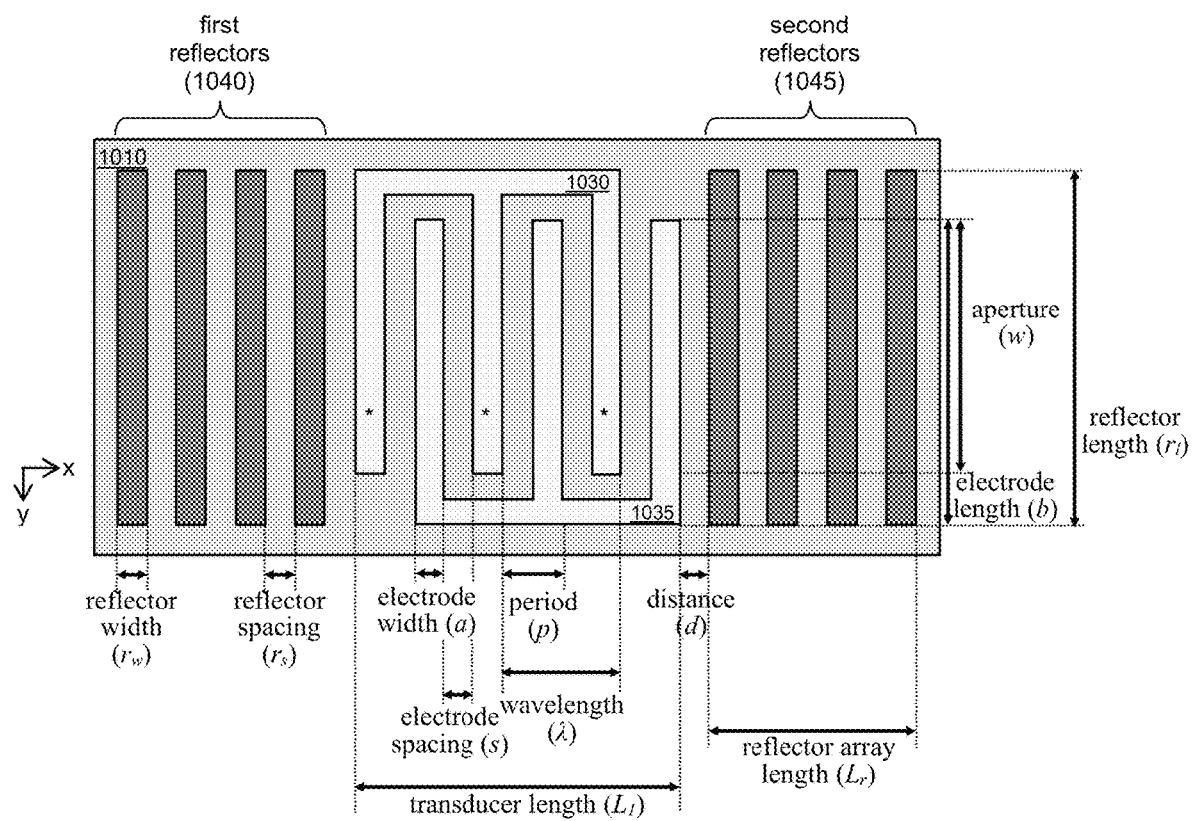

FIG. 19D provides dimensions of the electrode regions and reflector regions that can be optimized. For instance, the electrode region (including the first and second electrodes 1030,1035) and the reflector regions (including the first and second reflectors 1040,1045) can be arranged on the substrate 1010 in any useful manner.

The dimensions of the electrode region include a length of the electrode region or transducer length $L_1$ (e.g., of from about $10\lambda$ to about $500\lambda$, such as of from $50\lambda$ to $500\lambda$ or $100\lambda$ to $500\lambda$); a spacing $L_2$ between two electrode regions (e.g., as in FIG. 20, in which $L_2$ can be of from about $10\lambda$ to about $500\lambda$, such as of from $50\lambda$ to $500\lambda$ or $100\lambda$ to $500\lambda$); and an aperture w along a length of an electrode region or a dimension that is perpendicular to the propagation direction (e.g., an aperture w along the y-axis), in which w is of from about $20\lambda$ to about $500\lambda$.e.g., such as from $20\lambda$ to $100\lambda$, and/or of from about 10 μm to about 500 μm (e.g., such as from $50\lambda$ to $500\lambda$ or from $100\lambda$ to 500 μm). Other dimensions include those for individual electrodes or electrode fingers, such as an electrode width a along the propagation direction (e.g., along the x-axis, in which a is a width of $\lambda/8$, $\lambda/4$, $3\lambda/8$, or $\lambda/2$). In various embodiments, a has a width ranging from about 1 μm to about 4 μm; an electrode spacing s along the propagation direction (e.g., along the x-axis) and between the individual electrodes or individual electrode fingers (e.g., such as s=a, n×a, or a/n, in which n=1, 2, 3, ... m); a period p along the propagation direction (e.g., along the x-axis, in which p=a+s; or in which p is of from about 2 µm to about 100 µm); an acoustic wavelength λ (e.g., in which λ=2p or, when a=s, then λ=4a); an electrode length b (e.g., along the y-axis, such as of from about 50 µm to about 1000 µm; and/or of from about 20λ to about 500λ); a thickness $t_e$ of the electrode (e.g., along the z-axis, where the normalized thickness of the electrode is determined as $t_e/λ$, which can be of from about 1% to about 6%, such as from 3% to 6%); and an $n_e$ number of individual electrodes or $n_e$ number of pairs of electrodes, such as in an interdigitated transducer, in which $n_e$ is any number of from about 0.5 to about 500.

The electrode region can be configured to provide the operating frequency of the transducer, in which operating frequency $f_o=v_s/λ$, where $v_s$ is the shear velocity of the SH wave (e.g., of from about 3000 m·s$^{-1}$ to 6000 m·s$^{-1}$, such as about 4000 m·s$^{-1}$) and λ is the acoustic wavelength λ. The acoustic wavelength λ, in turn, can be determined lithographically. For instance, λ is generally twice the characteristic period of the electrode or electrode array (e.g., λ=2p), and this period p can be lithographically defined by patterned interdigitated electrodes having a particular electrode width a and electrode spacing s (e.g., p=a+s). The shear velocity $v_s$ is determined by the underlying substrate, as well as any overlying layers (e.g., guide layers).

The resonator can be configured to operate at any useful frequency $f_o$. Useful frequencies can include frequencies from about 80 MHz to about 3 GHz, such as of from 80 MHz to 200 MHz, 80 MHz to 300 MHz, 80 MHz to 375 MHz, 80 MHz to 450 MHz, 80 MHz to 600 MHz, 80 MHz to 750 MHz, 80 MHz to 1 GHz, 80 MHz to 2 GHz, 80 MHz to 2.5 GHz, 100 MHz to 200 MHz, 100 MHz to 300 MHz, 100 MHz to 375 MHz, 100 MHz to 450 MHz, 100 MHz to 600 MHz, 100 MHz to 750 MHz, 100 MHz to 1 GHz, 100 MHz to 2 GHz, 100 MHz to 2.5 GHz, 100 MHz to 3 GHz, 200 MHz to 300 MHz, 200 MHz to 375 MHz, 200 MHz to 450 MHz, 200 MHz to 600 MHz, 200 MHz to 750 MHz, 200 MHz to 1 GHz, 200 MHz to 2 GHz, 200 MHz to 2.5 GHz, 200 MHz to 3 GHz, 350 MHz to 450 MHz, 350 MHz to 600 MHz, 350 MHz to 750 MHz, 350 MHz to 1 GHz, 350 MHz to 2 GHz, 350 MHz to 2.5 GHz, 350 MHz to 3 GHz, 400 MHz to 450 MHz, 400 MHz to 600 MHz, 400 MHz to 750 MHz, 400 MHz to 1 GHz, 400 MHz to 2 GHz, 400 MHz to 2.5 GHz, 400 MHz to 3 GHz, 425 MHz to 450 MHz, 425 MHz to 600 MHz, 425 MHz to 750 MHz, 425 MHz to 1 GHz, 425 MHz to 2 GHz, 425 MHz to 2.5 GHz, 425 MHz to 3 GHz, 450 MHz to 600 MHz, 450 MHz to 750 MHz, 450 MHz to 1 GHz, 450 MHz to 2 GHz, 450 MHz to 2.5 GHz, 450 MHz to 3 GHz, 475 MHz to 600 MHz, 475 MHz to 750 MHz, 475 MHz to 1 GHz, 475 MHz to 2 GHz, 475 MHz to 2.5 GHz, 475 MHz to 3 GHz, 500 MHz to 600 MHz, 500 MHz to 750 MHz, 500 MHz to 1 GHz, 500 MHz to 2 GHz, 500 MHz to 2.5 GHz, 500 MHz to 3 GHz, 550 MHz to 600 MHz, 550 MHz to 750 MHz, 550 MHz to 1 GHz, 550 MHz to 2 GHz, 550 MHz to 2.5 GHz, 550 MHz to 3 GHz, 600 MHz to 750 MHz, 600 MHz to 1 GHz, 600 MHz to 2 GHz, 600 MHz to 2.5 GHz, or 600 MHz to 3 GHz. In alternative embodiments, the frequency $f_o$ is limited by lithographic limits (e.g., up to about 2.5 GHz, in one or more embodiments).

The electrode region(s) and reflector region(s) can be configured to optimize acoustic cavity performance. These regions can be designed for optimum coupling between the spatial periodic electrical field that accompanies the acoustic standing wave. For instance, the electrode region can be optimized by centering each electrode at the peaks of the electromagnetic field, and the reflector region can be optimized by ensuring that the Bragg frequency of the reflectors is substantially similar to the transducer frequency. Reflectors can be characterized by a Bragg frequency $f_B$, at which $λ_B=2p$, where p is the period for the reflectors (e.g., $p=r_s$ or $p=r_s+r_w$). In yet another instance, resonant conditions can be attained when the ratio of the spacing $L_2$ between two transducer pairs and the Bragg wavelength $λ_B$ is a fractional integer (e.g., $L_2/λ_B=n/2+1/4$, in which n=1, 2, 3, ... m).

The dimensions of the reflector region include a length of the reflector region or reflector array length $L_r$ (e.g., of from about 100 µm to about 1000 µm); a reflector width $r_w$ along the propagation direction (e.g., along the x-axis); a reflector spacing $r_s$ along the propagation direction (e.g., along the x-axis) and between the individual reflectors; a reflector length $r_l$ (e.g., along the y-axis, such as of from about 50 µm to about 500 µm; and/or of from about 20λ to about 50λ); a thickness $t_r$ of the reflector (e.g., along the z-axis, in which in some non-limiting embodiments, $t_r=t_e$); a center-to-center distance between two reflector regions (e.g., of from about 150λ to about 300λ); and an $n_r$ number of individual reflectors or $n_r$ number of pairs of reflectors, such as in an interdigitated reflector, in which $n_r$ is any number of from about 0.5 to about 500. In addition, the distance d between the electrode region and the reflector region can be any useful distance, e.g., a multiple of the acoustic wavelength λ, λ/8, λ/4, or λ/2, such as nλ/2, nλ/8, (2n+1)λ/8, (2n−1)λ/4, (4n+1)λ/8, or (4n+3)λ/8, in which n=1, 2, 3, ... m; or in which the distance is of from about 0.1λ to about 3λ.

FIG. 20 shows a resonator 200 having a two-port configuration, in which the electrode region and reflector regions are disposed on a substrate 210. The resonator 200 includes an electrode region, which in turn includes a first pair of transducer (having first and second electrodes 230, 235) and a second pair of transducers (having third and fourth electrodes 231,236). The electrode region also includes a spacing $L_2$ located between the first and second pairs of transducers. This spacing $L_2$ can be of any useful dimension that is, e.g., sufficient to efficiently propagate an acoustic wave with minimal loss, to maintain an acoustic cavity, to accommodate a fluid sample, to bind to a sufficient surface concentration of capture agents, and/or to capture a sufficient mass of a desired target. For this two-port configuration, the first and second reflectors 240,245 can be of any useful distance d between the electrode region and each of the first and second reflector regions.

Yet other resonators and components thereof are described in U.S. Pat. Nos. 5,073,763, 6,777,855, 7,173,360, 7,878,063, 8,436,509, 8,669,688, 8,709,791, 9,512,421, 10,031,135, and 10,261,078, each of which is incorporated herein by reference in its entirety.

Piezoelectric Substrate

The piezoelectric substrate can include any useful piezoelectric material. Exemplary piezoelectric materials include lithium tantalate ($LiTaO_3$), lithium niobate ($LiNbO_3$), potassium niobate ($KNbO_3$), quartz ($SiO_2$, such as an α-$SiO_2$), langatate ($La_3Ga_{5.5}Ta_{0.5}O_{14}$), langasite ($La_3Ga_5SiO_{14}$), langanite ($La_3Ga_{5.5}Nb_{0.5}O_{14}$), lead zirconate titanate ($PbZr_xTi_{1-x}O_3$, where 0≤x≤1, such as $PbZr_{0.52}Ti_{0.48}O_3$), cadmium sulfide (CdS), berlinite ($AlPO_4$), gallium phosphate ($GaPO_4$), lithium iodate ($LiIO_3$), lithium tetraborate ($Li_2B_4O_7$), bismuth germanium oxide ($Bi_{12}GeO_{20}$), zinc oxide (ZnO), aluminum nitride (AlN), etc., provided in any useful orientation, e.g., 36° YX $LiTaO_3$, Y+36° cut $LiTaO_3$, 0° X-cut LiTaO$_3$, 128° XY LiNbO$_3$, 41° YX LiNbO$_3$, 64° YX LiNbO$_3$, rotated Y-cut quartz, ST-X cut quartz, or 36° Y quartz.

In some embodiments, the piezoelectric substrate is obtained from a particular crystal cut that propagates and supports SH waves or leaky SH waves. In other embodiments, the electrode region is arranged on that particular crystal cut of the piezoelectric substrate to effectively launch the SH wave. In other embodiments, the piezoelectric substrate includes a piezoelectric crystal layer that is approximately thicker than the Love wave penetration depth, in which the crystal layer is optionally disposed on a non-piezoelectric substrate. Such piezoelectric substrate can include one or more electrode regions (e.g., any described herein), in which the components of the electrode regions are arranged to provide a useful acoustic propagation path along any directional axis that provides a useful acoustic wave (e.g., an SH acoustic wave).

A layer (e.g., a guide layer or a surface modified layer) can overlie a top surface of the piezoelectric substrate, or a portion of this top surface. Such a layer can be used for any useful purpose, e.g., to propagate a Love wave confined to that layer, to present one or more capture agents to a sample, and/or to provide a plurality of immobilized cells (e.g., bacterial cells) to a sample. The layer can be formed of any useful material, such as a polymer (e.g., a polystyrene, a polyimide, a polynorbornene, a perfluoropolymer, a poly(xylylene) (e.g., parylene C or poly(chloro-p-xylylene)), poly(dimethylsiloxane), or a polymethylmethacrylate (PMMA)), an oxide (e.g., ZnO), a silane, or a dielectric (e.g., a silicon oxide, such as SiO$_2$; a silicon oxynitride, e.g., SiON; or a silicon nitride, such as Si$_3$N$_4$, which can optionally including one or more dopants). The layer can be of any useful thickness, such as of from about 0.05 μm to about 20 μm (e.g., from 0.05 μm to 1 μm, 0.05 μm to 2 μm, 0.05 μm to 5 μm, 0.05 μm to 10 μm, 0.1 μm to 1 μm, 0.1 μm to 2 μm, 0.1 μm to 5 μm, 0.1 μm to 10 μm, 0.1 μm to 20 μm, 0.5 μm to 1 μm, 0.5 μm to 2 μm, 0.5 μm to 5 μm, 0.5 μm to 10 μm, 0.5 μm to 20 μm, 1 μm to 2 μm, 1 μm to 5 μm, 1 μm to 10 μm, 1 μm to 20 μm, 2 μm to 5 μm, 2 μm to 10 μm, 2 μm to 20 μm, 5 μm to 10 μm, or 5 μm to 20 μm).

Any method known in the art for depositing a layer may be used, e.g., such as plasma enhanced chemical vapor deposition. On top of the layer, a thin layer of a non-reactive liquid silicone material (e.g., a hexamethyldisilazane, oligodialkylsiloxane, polydialkylsiloxane, or other silicone, such any silanizing compound described herein) or any other non-reactive liquid may be used to prepare the surface for further functionalization. The layer, or a portion thereof, can include one or more linkers, binding agents, cells, and/or capture agents (e.g., any described herein).

Electrode Region

The electrode region can include any number of electrical components configured to deliver an electrical signal to the piezoelectric substrate, in which that electrical signal is transduced to provide an acoustic wave. The electrode region can include one or more electrodes configured in any useful manner. The electrodes can form a delay line, which can be optionally shorted. In addition, such lines can be unidirectional or bidirectional. The electrodes can be of any useful configuration (e.g., an interdigitated configuration, an arrayed configuration, a gate configuration, a one-port configuration, a two-port configuration, a delay line configuration, a unidirectional configuration, a bidirectional configuration, etc.), geometry (e.g., bar electrodes, single finger electrodes, double finger electrodes, split finger electrodes, pruned double split finger electrodes, etc.), orientation (e.g., having a major axis that is orthogonal to a first direction that is the propagate direction of the acoustic wave and/or configured to provide an acoustic wave along a crystal cut or axis that supports SH waves), or electrical connection (e.g., shorted, grounded, open, closed, arrayed, etc.).

Each port can include any useful electrode configuration. In one instance, each port can include a first electrode (e.g., an active electrode) and a second electrode (e.g., a ground electrode). In a one-port configuration, the first port includes a first electrode and a second electrode, in which the first electrode is active and the second electrode is grounded. An applied voltage results in an acoustic wave that is transmitted from the first electrode and received by the second electrode. In a two-port configuration, a first port includes a first electrode and a second electrode, and a second port includes a third electrode and a fourth electrode. A spacing L$_2$ is present between the first and second ports. In use, an applied voltage between the electrodes of the first port results in an acoustic wave, which propagates through the spacing L$_2$ of the piezoelectric substrate. This wave is then received by the second port. In some instances, the first and second ports are different. In other instances, the first and second ports are identical.

Electrodes can have any useful configuration. In one instance, the electrodes form an interdigitated transducer (IDT), in which the fingers of each electrode are interdigitated. The design of the IDT can be selected from single finger electrodes, double split finger electrodes, pruned double split finger electrodes, or unidirectional electrodes. For instance, FIG. 19D shows an IDT including single finger electrodes 1030,1035, in which these electrodes are interdigitated. The electrodes have a single finger configuration, as seen by the presence of one electrode finger in each period p.

In another instance, the IDT includes a pair of opposing comb-shaped electrodes (a first electrode and a second electrode), each electrode having a fingerlike periodic pattern of electrode fingers interdigitated with the electrode fingers of the opposing comb-shaped electrode. An acoustic cell within the IDT is defined in terms of the periodicity p of the finger structure that is specified in terms of the acoustic wavelength λ. This cell pattern often repeats for a specific number of wavelengths which defines the overall acoustic length of the IDT. When a RF drive voltage is applied to the comb-shaped electrodes of the transmitting IDT, a spatially periodic, surface-concentrated electric field distribution is established between the spatially periodic electrode fingers that penetrate into the piezoelectric substrate. Because of the piezoelectric coupling, an elastic strain distribution with periodicity is created in the substrate, thereby generating the acoustic wave. To generate the correct acoustic wave, the proper axis of the piezoelectric crystal is preferably aligned with the IDT. The strength of the outputted acoustic wave can be controlled by changing the overlap of the electrodes as determined by an aperture w, a number n$_e$ of finger pairs, their periodic p, the finger pattern, and the power input.

Other exemplary electrode configurations include one or more double split finger electrodes, pruned double split finger electrodes, single-phase unidirectional transducers (SPUDTs), a double-metallization SPUDT structure, a natural SPUDT (NSPUDT), or an electrode-width-controlled SPUDT (EWC-SPUDT). Yet other electrode configurations are described in U.S. Pat. Nos. 5,073,763, 6,777,855, 7,173,360, 7,878,063, 8,436,509, 8,669,688, and 10,261,078, each of which is incorporated herein by reference in its entirety.

The transducer length $L_1$ for each port (or electrode pair) can be of any useful dimension. In one instance, $L_1$ is determined based on a multiple of the characteristic acoustic wavelength $\lambda$. Exemplary $L_1$ includes of from about 10 to about 500$\lambda$ (e.g., about 197$\lambda$, or from 50$\lambda$ to 500$\lambda$). Each transducer can include any useful number $n_e$ of fingers or finger pairs, such as of from about 10 to 500 fingers or finger pairs (e.g., from 20 to 500 fingers or finger pairs). The period p can be of any useful dimension, such as of from about 2 μm to about 100 μm (e.g., of from 2 μm to 90 μm, 2 μm to 75 μm, 2 μm to 50 μm, 2 μm to 40 μm, 2 μm to 25 μm, 2 μm to 10 μm, 5 μm to 100 μm, 5 μm to 90 μm, 5 μm to 75 μm, 5 μm to 50 μm, 5 μm to 40 μm, 5 μm to 25 μm, 5 μm to 10 μm, 8 μm to 100 μm, 8 μm to 90 μm, 8 μm to 75 μm, 8 μm to 50 μm, 8 μm to 40 μm, 8 μm to 25 μm, 8 μm to 10 μm, 10 μm to 100 μm, 10 μm to 90 μm, 10 μm to 75 μm, 10 μm to 50 μm, 10 μm to 40 μm, 10 μm to 25 μm, 15 μm to 100 μm, 15 μm to 90 μm, 15 μm to 75 μm, 15 μm to 50 μm, 15 μm to 40 μm, 15 μm to 25 μm, 20 μm to 100 μm, 20 μm to 90 μm, 20 μm to 75 μm, 20 μm to 50 μm, 20 μm to 40 μm, 20 μm to 25 μm, 25 μm to 100 μm, 25 μm to 90 μm, 25 μm to 75 μm, 25 μm to 50 μm, 25 μm to 40 μm, 30 μm to 100 μm, 30 μm to 90 μm, 30 μm to 75 μm, 30 μm to 50 μm, or 30 μm to 40 μm, such as about 10 μm). For each transducer, the metallization ratio $\eta$ can be determined as a ratio of the electrode width a to the period p, and this ratio can be any useful value (e.g., $\eta=a/p$ of from about 0.4 to about 0.75).

The aperture w for each port (or electrode pair) can be of any useful dimension. In one instance, aperture w is determined based on a multiple of the characteristic acoustic wavelength $\lambda$. Exemplary w includes of from about 10$\lambda$ to about 200$\lambda$ (e.g., about 10$\lambda$ to about 50$\lambda$); or from about 10 μm to about 500 μm (e.g., about 50 μm, 100 μm, or 200 μm, such as about 50 μm to 250 μm). The characteristic wavelength can be of from about 10 μm to 100 μm (e.g., from 10 μm to 60 μm).

The electrodes can be formed of any suitable conductive material. Exemplary materials include aluminum, gold, chromium, silver, tantalum, tungsten, with an optional adhesion layer (e.g., including titanium), as well as alloys thereof and annealed forms thereof. In addition, each electrode can include one or more lines (e.g., bonding wires), which in turn may optionally be connected to one or more contacts (e.g., contact pads configured to provide an electrical connection to the electronics module).

Reflector Regions

The resonator can include one or more reflector regions configured to support an acoustic cavity. Such reflector regions can include one or more electrodes (e.g., any configuration or design described herein) that are grounded and/or shorted. In some embodiments, the reflector region includes an array of reflectors, where any number of reflectors $n_r$ may be present in the array (e.g., of from about 10 to about 500). Furthermore, each reflector can have any useful dimension (e.g., any useful reflector length $r_1$ or reflector width $r_w$), configuration (e.g., any useful reflector spacing $r_s$ or number of reflectors $n_r$), or design (e.g., a bar electrode, a strip electrode, a grating design, etc.).

Exemplary reflectors can include an array of bar reflectors. Each reflector can have any useful reflector length $r_1$ (e.g., such as of from about 50 μm to about 500 μm), reflector width $r_w$ (e.g., such as a multiple of the acoustic wavelength $\lambda$, $\lambda/8$, $\lambda/4$, or $\lambda/2$, such as $n\lambda/2$, $n\lambda/8$, $(2n+1)\lambda/8$, $(2n-1)\lambda/4$, $(4n+1)\lambda/8$, or $(4n+3)\lambda/8$, in which n=1, 2, 3, . . . m; and/or of from about 10 nm to about 250 μm, such as of from 0.5 μm to 100 μm), or reflector spacing $r_s$ (e.g., such as $r_s=r_w$, $n \times r_w$, or $r_w/n$, in which n=1, 2, 3, . . . m). Yet other configurations include a grating design, in which the individual reflectors are connected by a bar section to form a grating. Another configuration includes a stub section. Alternatively, each reflector region can include two or more reflectors.

The reflectors can be formed of any useful material, including, but not limited to, aluminum, gold, chromium, silver, platinum, tungsten, with an optional adhesion layer (e.g., including titanium), as well as alloys thereof. In one non-limiting example, the reflectors are composed of the same material as the electrodes, e.g., to simplify fabrication of the resonator.

Functionalized Active Area

The functionalized area can include any useful combination of agents, including cells or other capture agents (e.g., any described herein) configured to bind one or more targets (e.g., compounds, such as antibiotic compounds). In addition, the functionalized active area is located in a region of the resonator to facilitate sensitive detection of any mass changes occurring in this area. In one instance, the functionalized active area is disposed in proximity to (e.g., above) the acoustic cavity. Furthermore, the functionalized active area can include a portion of the guide layer within the acoustic cavity.

The functionalized active area can have any useful dimension. For instance, in a one-port configuration, one dimension of the active area is determined by the transducer length $L_1$. In another instance, in a two-port configuration, one dimension of the active area is determined by the spacing $L_2$ between two transducer pairs. Each of $L_1$ and $L_2$ can have any useful dimension, such as of from about 50$\lambda$ to about 500$\lambda$ (e.g., of from 50$\lambda$ to 200$\lambda$) and/or of from about 50 μm to about 800 μm. In another instance, a second dimension of the active area is determined by the electrode length b (e.g., any described herein, such as of from about 50 μm to about 500 μm). In yet another instance, $L_1$ and $L_2$ is less than the length of the reflector region $L_r$ to suppress ripples (e.g., a ratio $L_r/L_1$ or $L_r/L_2$ of from about 2 to about 10). Other exemplary reflector region designs are described in U.S. Pat. Nos. 4,837,476, 6,848,295, 7,500,379, 7,679,474, 9,048,807, and 10,261,078, as well as U.S. Pub. No. 2009/0282902, each of which is incorporated herein by reference in its entirety.

In addition, to ensure selective detection of the desired target, the functionalized active area can include one or more capture agents configured to bind one or more targets. Any useful capture agent can be employed, e.g., cells, antibodies, proteins, etc., such as any described herein. Further, the agent can be directly or indirectly attached to a surface using covalent bonds and/or non-covalent bonds (e.g., via van der Waals forces, hydrogen bonds, and/or other intermolecular forces). For direct attachment, the agent can be adsorbed to the surface or reacted with a functional group present on the surface. For indirect attachment, the agent can be attached to a linker (e.g., any described herein), and this linker can in turn be directly or indirectly attached to the surface.

The surface can be a portion of a layer within the acoustic cavity. This surface can be treated in any useful manner to allow for direct or indirect attachment of a capture agent. The surface can be treated to provide a reactive group or a reactive layer. For instance, if the surface includes siloxane (Si—O—Si) bonds, then the surface can be oxidized to provide reactive silanol (Si—O—H) bonds.

In another instance, the surface can be treated with one or more binding agents that in turn provide a reactive group or a reactive layer (e.g., a reactive layer including an epoxide group, an amino group, a hydroxyl group, an alkoxy group, etc.). If the surface is treated to include a reactive layer having an epoxide group, then one or more capture agents having a nucleophile (e.g., an amino group) can be employed in a ring-opening reaction with the epoxide, thereby covalently attaching that capture agent to the surface by way of the reactive layer. One or more reactive layers can be employed on the surface to attach one or more linkers (e.g., between the surface and the capture agent, between the binding agent and the capture agent, and/or between the surface and the binding agent), binding agents (e.g., an agent configured to bind to a capture agent, or a portion thereof, to facilitate immobilization of the capture agent to the surface), and/or capture agents to the surface.

In one non-limiting example, the capture agent is a cell (e.g., a mammalian cell, a bacterial cell, etc.), and the surface of the active area includes a plurality of such immobilized cells. Immobilization can be facilitated by employing any useful methodology (e.g., any described herein).

In another non-limiting example, the capture agent can be a labeled protein, and the surface of the active area can include a linker that binds the label of the labeled protein. For instance, if the capture agent is a biotinylated antibody, then the surface can include a linker having an avidin (or a modified version of the avidin protein) that binds biotin. In another non-limiting example, the capture agent can be a labeled protein, and the surface includes a reactive layer configured to attach a binding agent that reacts with the capture agent. For instance, if the capture agent is a biotinylated antibody and the binding agent is an avidin, then the reactive layer can be an epoxide that reacts with amino groups present on avidin. In yet another instance, if the capture agent is an antibody, then the binding agent can be an immunoglobulin-binding protein (e.g., protein G, protein A, or protein L, as well as recombinant forms thereof, such as protein A/G) that binds to the Fab, L, and/or Fc regions of antibodies. In this instance, the binding agent can be directly attached to the surface (e.g., by way of physical adsorption) or indirectly attached by way of one or more reactive layers that attach to the binding agent.

To facilitate binding of the capture agents to the functionalized active area, any useful methodology and/or agent(s) can be employed. In one instance, the capture agent is physically adsorbed to the functionalized active area. In another instance, a covalent bond is present between the capture agent and a surface of the resonator (e.g., a surface of the guide layer).

In yet another instance, a covalent bond is present between the capture agent and a binding agent, in which this binding agent in turn is attached directly or indirectly to the surface of the resonator. The binding agent can include any useful compound, including linkers (e.g., any described herein), lipid layers (e.g., including bilipid layers having any useful lipophilic component, such as cholesterol), silanizing compounds (e.g., any described herein), and/or self-assembled monolayers (e.g., one or more thiols disposed on a metal (e.g., gold or silver) layer, in which this metal layer is disposed on the guide layer of the resonator; and the one or more thiols can be functionalized to be attached to a capture agent). Any useful combination of linkers, capture agents, binding agents, and reactive layers can be employed to provide the functionalized active area.

Electronics Module

The electronics module can provide one or more electrical connections to the resonator (e.g., the electrode region of the resonator). In particular, the electronics module can include a portion (e.g., a recessed portion) configured to accommodate the resonator (e.g., active resonator and inactive resonator), as well as include one or more electrical connections (e.g., pins, connectors, etc.) to the bond pad(s), contact pad(s), bond line(s), electrode(s), and reflector(s).

The electronics module can include any useful circuit components, such as an oscillator circuit (e.g., any described herein, as well as a Pierce circuit, a Colpitts circuit, or a Clapp circuit including an amplifier or a transistor, such as a bipolar junction transistor); one or more attenuation networks (e.g., including one or more circuit components to reduce the amplitude of a signal, such as by use of one or more resistors); one or more filters (e.g., a frequency selective, a high pass filter, a low pass filter, or a phase shifting filter); one or more amplifiers (e.g., transistors); one or more impedance matching networks (e.g., including one or more circuit components configured to match the impedance of the resonator to another electronic component, in which exemplary impedance matching networks can include an inductor with an optional resistor in series with the non-grounded electrode(s) of the resonator); and/or one or more coupling networks (e.g., configured to provide an output, such as a measured frequency shift).

A desired output (e.g., a frequency shift) can be measured in any useful manner, such as by an oscillator circuit. Any useful oscillator circuit can be employed to detect the one or more outputs. Exemplary circuits, components, and methodologies are described in U.S. Pat. Nos. 3,836,873, 3,878,481, 4,570,132, 5,416,448, 6,169,459, 6,169,461, 6,624,708, or 9,627,602 and U.S. Pat. Pub. Nos. 2006/0055480 or 2006/0114072, as well as Kelly R D, "Electronic circuit analysis and design by driving-point impedance techniques," *IEEE Trans. Educ.* 1970; E-13:154-67; Martin S J et al., "Resonator/oscillator response to liquid loading," *Sandia Report No. SAND97-0124J*, 1997 (26 pp.); Martin S J et al., "Sensing liquid properties with thickness-shear mode resonators," *Sandia Report No. SAND94-0079J*, 1993 (36 pp.); Martin S J et al., "Sensing in liquids using quartz resonators: mass accumulation and liquid properties," *Sandia Report No. SAND93-0311A*, 1993 (1 p.); Spates J J et al., "Resonator/oscillator response to liquid loading," *Sandia Report No. SAND94-1310C*, 1994 (11 pp.); Wessendorf K O, "Driving point impedance circuit analysis techniques," *Sandia Report No. SAND92-2832C*, 1993 (81 pp.); Wessendorf K O, "High-frequency voltage-controlled-oscillator for use with inverted-mesa quartz resonators," *Sandia Report Nos. SAND96-0019A*, 1996 (1 p.) and *SAND96-0019C*, 1996 (9 pp.); Wessendorf K et al., "Oscillator design techniques allow high-frequency applications," *Sandia Report No. SAND98-1839J*, 1998 (6 pp.); Wessendorf K et al., "Oscillator design techniques allow high frequency applications of inverted mesa resonators," sss-mag.com/pdf/saosc.pdf (8 pp.); Wessendorf K O, "Quartz oscillator analysis," *Sandia Report No. SAND87-0311*, 1988 (31 pp.); Wessendorf K O, "The active-bridge oscillator," *Sandia Report Nos. SAND98-0203A*, 1998 (1 p.) and *SAND98-1558C*, 1998 (9 pp.); Wessendorf K O, "The active-bridge oscillator for use with liquid loaded QCM sensors," *Sandia Report No. SAND2001-0097A*, 2001 (1 p.); Wessendorf K O, "The active-bridge oscillator for use with liquid loaded QCM sensors," *Sandia Report No. SAND2001-1944C*, 2001 (6 pp.); and Wessendorf K O, "The Lever oscillator for use in high resistance resonator applications," *Sandia Report No. SAND93-0145C*, 1993 (7 pp.), each of which is incorporated herein by reference in its entirety.

In one instance, an output of the resonator is connected to the gain device (e.g., an amplifier, such as a bipolar junction transistor), and the output of the gain device is connected to its input. In this way, an oscillating signal is established, which in turn can be used to resolve the resonant frequency shift of the resonator. In use, a change in mass (resulting from binding a target) shifts the resonant frequency of the resonator, and this shift in resonant frequency can be detected with an oscillator circuit.

Additional electronic components can include a frequency mixer, a frequency doubler, a frequency demultiplier, a frequency counter, a network analyzer, a capacitor, a transistor, etc., in which any components can be provided in any useful manner (e.g., as an integrated circuit). Other design considerations are described in Schmitt R F et al., "Rapid design of SAW oscillator electronics for sensor applications," *Sens. Actuat. B* 2001; 76:80-5; Martin S J et al., "Characterization of SH acoustic plate mode liquid sensors," *Sens. Actuat.* 1989; 20:253-68; and Grate J W et al., "Acoustic wave microsensors," *Anal. Chem.* 1993; 65(21):940A-8A, each of which is incorporated herein by reference in its entirety.

Fluidics Module

The fluidics module can include any useful port, via, chamber, and/or channel to deliver a sample to the functionalized active area of the resonator. The fluidics module may be configured to be a disposable manifold that aligns with the resonator and the electronics module. Alternatively, the fluidics module may be reusable for repeat use. The fluidics module can optionally include any useful microfluidic structure having a length, width, height, cross-sectional dimension, circumference, radius (e.g., external or internal radius), or diameter that is less than 1 mm. An exemplary fluidics module can include a fluidics layer configured to be in fluid communication with a functionalized active area of the resonator. For instance, the fluidics layer can include a sample chamber designed to overlie the functionalized active area.

Capture Agents

Any useful capture agents can be used in combination in the present application. The capture agent can directly or indirectly bind the marker of interest. Further, multiple capture agents (e.g., optionally employed with one or more linkers and/or binding agents) can be used to bind the target and provide a detectable signal for such binding.

Exemplary capture agents include one or more of the following: a cell that binds to or interacts with a compound, such as a mammalian cell, a plant cell, an algal cell, a bacterial cell, etc.; a protein that binds to or detects one or more targets (e.g., an antibody including monoclonal or polyclonal forms thereof, an affibody, an enzyme, or fragments or recombinant forms of any of these), a globulin protein (e.g., bovine serum albumin), an amino acid, a peptide (e.g., a polypeptide, including modified forms thereof, such as glycosylated polypeptides or multimeric polypeptides), a polysaccharide (e.g., a cyclic polysaccharide), a nucleic acid (e.g., a nucleotide, a single stranded DNA, a single stranded RNA, and an oligonucleotide, including modified forms of any of these), a nanoparticle, a microparticle, a sandwich assay reagent, a label (e.g., one or more fluorescent labels, colorimetric labels, quantum dots, nanoparticles, microparticles, barcodes, radio labels (e.g., RF labels or barcodes), avidin, biotin, tags, dyes, an enzyme that can optionally include one or more linking agents and/or one or more dyes, as well as combinations thereof), a catalyst (e.g., that reacts with one or more targets), a lipid (e.g., a glycosylated lipid), and/or an enzyme (e.g., that reacts with one or more targets, such as any described herein). The capture agent can optionally include one or more labels, e.g., any described herein. In particular embodiments, more than one capture agent, optionally with one or more linking agents, can be used to detect a target of interest.

Optionally, linking agents can be used to attach the capture agent to the surface. Exemplary linking agents include compounds including one or more first functional groups, a linker, and one or more second functional groups. In some embodiments, the first functional group allows for linking between a surface and the linker (e.g., by way of a covalent or a non-covalent bond), and the second functional group allows for linking between the linker and the agent (e.g., a capture agent, a binding agent, a label, or any agent described herein, and by way of a covalent or a non-covalent bond). Exemplary linkers include any useful linker, such as polyethylene glycol (e.g., $(CH_2CH_2O)_{mg}$, where mg is from 1 to 50), an alkylene group (e.g., an optionally substituted $C_{1-12}$ alkylene or alkynyl chain), a heteroalkylene group, a carbocyclic ring (e.g., an aromatic ring, such as a phenyl group), a polypeptide (e.g., a dipeptide, tripeptide, etc.), and/or a flexible arm, e.g., 2, 3, 4, 5, 6, 7, 8, 9, 10, 11, 12, 13, 14, or 15 carbon atoms. The first and second functional groups can include any useful chemical moiety, such as moieties from a click-chemistry reaction pair selected from the group consisting of a Huisgen 1,3-dipolar cycloaddition reaction between an alkynyl group and an azido group to form a triazole-containing linker; a Diels-Alder reaction between a diene having a 4π electron system (e.g., an optionally substituted 1,3-unsaturated compound, such as optionally substituted 1,3-butadiene, 1-methoxy-3-trimethylsilyloxy-1,3-butadiene, cyclopentadiene, cyclohexadiene, or furan) and a dienophile or heterodienophile having a 2π electron system (e.g., an optionally substituted alkenyl group or an optionally substituted alkynyl group); a ring opening reaction with a nucleophile and a strained heterocyclyl electrophile; and a splint ligation reaction with a phosphorothioate group and an iodo group; and a reductive amination reaction with an aldehyde group and an amino group Other exemplary linkers include BS3 ([bis(sulfosuccinimidyl)suberate]; BS3 is a homobifunctional N-hydroxysuccinimide ester that targets accessible primary amines, such as those present on proteins or antibodies), NHS/EDC (N-hydroxysuccinimide and N-ethyl-(dimethylaminopropyl)carbodiimide; NHS/EDC allows for the conjugation of primary amine groups with carboxyl groups), sulfo-EMCS ([N-e-maleimidocaproic acid]hydrazide; sulfo-EMCS are heterobifunctional reactive groups (maleimide and NHS-ester) that are reactive toward sulfhydryl and amino groups), hydrazide (most proteins contain exposed carbohydrates and hydrazide is a useful reagent for linking carboxyl groups to primary amines), and SATA (N-succinimidyl-S-acetylthioacetate; SATA is reactive towards amines and adds protected sulfhydryls groups).

In particular embodiments, the linking agent is a silanizing compound. Exemplary silanizing agents include silazane (e.g., hexamethyldisilazane (HMDS)), haloalkylsilane (e.g., methyltrichlorosilane, trichlorocyclohexylsilane, dichlorodimethylsilane, dichloroethylsilane, bromotrimethylsilane, or chlorotrimethylsilane), haloarylsilane (e.g., fluorotriphenylsilane), trialkylsilylsilane (e.g., chlorotris(trimethylsilyl)silane), and silanol (e.g., 2-(trimethylsilyl)ethanol). Other silanizing agents include an agent having the structure of $(R^L)_3SiR^M$ or $R^LSi(R^M)_3$ or $R^LSi(SiR^M)_3$ or $(R^L)_2R^MSi\text{-}L\text{-}SiR^M(R^L)_2$, where each of $R^L$ is, independently, H, optionally substituted alkyl, hydroxyl, hydroxyalkyl, halo, haloalkyl, alkoxy, or aryl; each of $R^M$ is, independently, a functional moiety, such as optionally substituted alkyl, haloalkyl, hydroxyalkyl, alkenyl, alkoxy, aryl, alkaryl, heterocyclyl, heteroaryl, cycloalkyl, alkcycloalkyl, amino, aminoalkyl, or amido; L is a linker, such as optionally substituted alkylene, alkyleneoxy, arylene, heteroalkylene, heteroalkyleneoxy, or —N(R$^{N1}$)—, where R$^{N1}$ is H, optionally substituted alkyl, alkaryl, or aryl; and where one of R$^L$ and X can optionally combine to form an optionally substituted heterocyclyl.

Such silanizing compounds can be used to graft an agent onto a surface (e.g., a silicon dioxide surface, or any surface including reactive hydroxyl groups). Other exemplary linking agents include pairs of linking agents that allow for binding between two different components. For instance, biotin and streptavidin react with each other to form a non-covalent bond, and this pair can be used to bind particular components.

Targets, Including Markers

The present device can be used to determine any useful targets or markers. Exemplary targets include a virus, a bacterium (e.g., an antibiotic resistant bacterium or an antibiotic susceptible bacterium), a pathogen, a cell (e.g., a eukaryotic cell, a prokaryotic cell, a spore, as well as whole cells or fragments thereof), a protein (e.g., a prion, a membrane protein, a peptide marker, a hormone, etc.), a modified protein (e.g., a glycosylated, aminated, peglylated, phosphorylated, acetylated, truncated, or mutated protein), a peptide, a nucleic acid (including a nucleotide or a polynucleotide, e.g., DNA, RNA, mRNA, rTRNA, microRNA, etc., for detecting one or more alleles, pathogens, single nucleotide polymorphisms, mutations, etc.), a modified nucleic acid (e.g., a mutated nucleic acid), a cytokine (e.g., TNF-α, IL-12, or IL-1β), a prion, etc., as well as fragments or extracts of any of these. Additional targets, markers, and capture agents are described in U.S. Pat. No. 8,709,791, which is incorporated herein by reference in its entirety.

Exemplary targets include a bacterium, such as *Bacillus* (e.g., *B. anthracis*), Enterobacteriaceae (e.g., *Salmonella, Escherichia coli, Yersinia pestis, Klebsiella,* and *Shigella*), *Yersinia* (e.g., *Y. pestis* or *Y. enterocolitica*), *Staphylococcus* (e.g., *S. aureus* or *S. epidermidis*), *Streptococcus* (e.g., *S. pyogenes* or *S. pneumoniae*), *Gonorrhea, Enterococcus* (e.g., *E. faecalis* or *E. faecium*), *Listeria* (e.g., *L. monocytogenes*), *Acinetobacter* (e.g., *A. baumannii*), *Brucella* (e.g., *B. abortus, B. melitensis,* or *B. suis*), *Vibrio* (e.g., *V cholerae*), *Corynebacterium diphtheria, Pseudomonas* (e.g., *P. pseudomallei* or *P. aeruginosa*), *Klebsiella* (e.g., *K. pneumoniae*), *Burkholderia* (e.g., *B. mallei, B. cepacia,* or *B. pseudomallei*), *Shigella* (e.g., *S. dysenteriae*), *Rickettsia* (e.g., *R. rickettsii, R. prowazekii,* or *R. typhi*), *Francisella tularensis, Chlamydia psittaci, Coxiella burnetii, Clostridioides* (e.g., *C. difficile*), *Helicobacter* (e.g., *H. pylori*), *Haemophilus* (e.g., *H. influenza*), *Neisseria* (e.g., *N. gonorrhoeae*), *Providencia, Citrobacter, Morganella, Campylobacter, Proteus, Salmonella* (e.g., *S. typhi*), *Mycobacterium* (e.g., *M. tuberculosis*), *Serratia,* or *Mycoplasma* (e.g., *M. mycoides*), as well as antibiotic resistant forms thereof, such as ampicillin resistant, carbapenem resistant, cephalosporin resistant, third-generation cephalosporin resistant, clarithromycin resistant, fluoroquinolone resistant, methicillin resistant, penicillin resistant, vancomycin resistant, or multi-drug resistant forms of any of these; allergens, such as peanut dust, mycotoxins, mold spores, or bacterial spores such as *Clostridium botulinum* and *C. perfringens*; toxins, such as ricin, mycotoxin, tetrodotoxin, anthrax toxin, botulinum toxin, staphylococcal entertoxin B, or saxitoxin; a protozoon, such as *Cryptosporidium parvum, Encephalitozoa, Plasmodium, Toxoplasma gondii, Acanthamoeba, Entamoeba histolytica, Giardia lamblia, Trichomonas vaginalis, Leishmania,* or *Trypanosoma* (e.g., *T. brucei* and *T. Cruzi*); a helminth, such as cestodes (tapeworms), trematodes (flukes), or nematodes (roundworms, e.g., *Ascaris lumbricoides, Trichuris trichiura, Necator americanus,* or *Ancylostoma duodenale*); a parasite (e.g., any protozoa or helminths described herein); a fungus, such as *Aspergilli, Candidae, Coccidioides immitis,* and *Cryptococci*; an environmental contaminant; a water additive; an agricultural marker; a nucleic acid (e.g., oligonucleotides, polynucleotides, nucleotides, nucleosides, molecules of DNA, or molecules of RNA, including a chromosome, a plasmid, a viral genome, a primer, or a gene); a protein (e.g., a glycoprotein, a metalloprotein, an enzyme, a prion, or an immunoglobulin); a metabolite; a sugar; a lipid; a lipopolysaccharide; a salt; or an ion.

In some instances, the target includes a virus (e.g., animal, plant, fungal, and/or bacterial viruses), including Adenoviridae (e.g., adenovirus), Arenaviridae (e.g., Machupo virus), Astroviridae, Bunyaviridae (e.g., Hantavirus, Andes virus, Sin Nombre virus, and Rift Valley fever virus), Caliciviridae (e.g., Norwalk virus), Coronaviridae, Filoviridae (e.g., Ebola virus and Marburg virus), Flaviviridae (e.g., Japanese encephalitis virus, dengue virus, West Nile virus, and Yellow fever virus), Hepadnaviridae (e.g., hepatitis A virus, hepatitis B virus, and hepatitis C virus), Herpesviridae (e.g., Epstein-Barr virus and herpes simplex viruses, such as HSV-1 and HSV-2), Orthomyxoviridae (e.g., influenza viruses, such as influenza virus A (e.g., subtype H5N1, H3N2, or H1N1), influenza virus B, and influenza virus C), Papillomaviridae (e.g., human papilloma virus), Papovaviridae (e.g., papilloma viruses and polyomaviruses, such as Simian virus 40 (SV40)), Paramyxoviridae (e.g., respiratory syncytial virus, measles virus, mumps virus, and parainfluenza virus), Parvoviridae (e.g., adeno-associated virus), Picornaviridae (e.g., polioviruses, enteroviruses, rhinoviruses, hepatoviruses, and coxsackieviruses), Polyomaviridae, Poxviridae (e.g., variola viruses), Reoviridae (e.g., rotaviruses), Retroviridae (e.g., human T cell lymphotropic viruses (HTLV) and human immunodeficiency viruses (HIV), such as HIV-1 and HIV-2), Rhabdoviridae (e.g., rabies virus), and Togaviridae (e.g., encephalitis viruses and rubella virus).

Targets also include food-borne pathogens, such as *Salmonella* (e.g., *Salmonella Typhimurium*), pathogenic *E. coli* (e.g., O157:H7), *Bacillus* (e.g., *B. cereus*), *Clostridium botulinum, Listeria monocytogenes, Yersinia* (e.g., *Y. enterocolitica*), Norovirus (e.g., Norwalk virus), *Shigella, Staphylococcus aureus, Toxoplasma gondii, Vibrio* (e.g., *V vulnificus, V cholera, V. parahaemolyticus*), *Campylobacter jejuni,* and *Clostridium perfringens*; and weaponized pathogens, such as *Bacillus anthracis, Yersinia pestis, Francisella tularensis, Brucella* (e.g., *B. suis*), *Burkholderia mallei, Burkholderia pseudomallei, Shigella, Clostridium botulinum,* Variola (e.g., *V major*), Filoviridae (e.g., Ebola virus and Marburg virus), Arenaviridae (e.g., Lassa virus and Machupo virus), *Clostridium perfringens,* any food-borne pathogen (e.g., *Salmonella* species, *Escherichia coli* O 157:H7, or *Shigella*), *Chlamydia psittaci, Coxiella burnetii, Staphylococcal aureus, Rickettsia* (e.g., *R. prowazekii* or *R. rickettsii*), Alphavirus (e.g., Venezuelan equine encephalitis virus, eastern equine encephalitis virus, or western equine encephalitis virus), *Vibrio cholerae, Cryptosporidium parvum,* Henipavirus (e.g., Nipah virus), Bunyaviridae (e.g., Hantavirus or Rift Valley fever virus), Flaviviridae (e.g., Japanese encephalitis virus and Yellow fever virus), and *Coccidioides* spp.

Test Samples

The present system can be used to test any useful test sample, such as blood (e.g., whole blood), plasma, serum, transdermal fluid, interstitial fluid, sweat, intraocular fluid, vitreous humor, cerebrospinal fluid, extracellular fluid, lacrimal fluid, tear fluid, sputum, saliva, mucus, etc., and any other bodily fluid. The test sample can include any useful sample, such as a microorganism, a virus, a bacterium, a fungus, a parasite, a helminth, a protozoon, a cell, tissue, a fluid, a swab, a biological sample (e.g., blood, serum, plasma, saliva, etc.), an environmental sample, an agricultural sample, etc.

The sample can be obtained from any useful source, such as a subject (e.g., a human or non-human animal), a plant (e.g., an exudate or plant tissue, for any useful testing, such as for genomic and/or pathogen testing), an environment (e.g., a soil, air, and/or water sample), a chemical material, a biological material, or a manufactured product (e.g., such as a food or drug product).

Methods of Use

The present application also relates to methods of using a system to detect any useful target (e.g., an antibiotic resistant cell). In one non-limiting example, the method includes use of a test sample requiring minimal or no sample preparation. In another non-limiting example, the method includes label-free detection of the target.

In one embodiment, an exemplary method includes the steps of delivering a compound (e.g., a test compound, such as an antibiotic, an antimicrobial, an antiviral, a drug, a therapeutic, etc.) to a plurality of immobilized bacterial cells in an active area; and measuring an output signal of a frequency shift or an amplitude change of the active resonator. In some embodiments, the output signal is provided by an active shunt capacitance cancelling oscillator circuit (e.g., any described herein). In other embodiments, the oscillator circuit effectively cancels out a shunt capacitance associated with the active resonator. In yet other embodiments, the output signal indicates growth or inhibition of the plurality of immobilized bacterial cells In particular embodiments, the active area (e.g., a functionalized active area) is disposed in proximity to an acoustic cavity, and the acoustic cavity disposed within an active resonator is configured to store mechanical energy from an acoustic wave.

For any of the methods herein, the system or resonator can have any useful configuration described herein, such as any useful arrangement of electrode region(s) and reflector region(s), as well as any useful module (e.g., fluidic module and/or electronic module). In some embodiments, the resonator is configured to be connected to an oscillator circuit to facilitate measurement of frequency shifts. In the delivering step, any useful sample (e.g., a liquid sample) can be tested with the system. To detect the desired target, the sample can be delivered to an area of the resonator, and this area can include one or more capture agents that specifically bind to or interact with the desired target. The area (e.g., functionalized area) can be of any sufficient area to accommodate a minimized sample volume, while providing a large enough surface area to facilitate binding of multiple targets (e.g., a plurality of cells) to the area (e.g., to increase sensitivity of the biosensor).

The measuring step can include measuring any useful output signal (e.g., a shift in resonant frequency). Optionally, the method can include determining growth or inhibition of the plurality of immobilized bacterial cells based on the output signal. In one instance, the methodology includes applying a determined extracted slope from a mass-frequency plot (a slope of df/dm) to the measured frequency shift ($\Delta f$), thereby determining the mass change ($\Delta m$).

EXAMPLES

Example 1: Rapid Antimicrobial Susceptibility Determination Using Acoustic Resonance Acoustic wave devices continue to have wide-spread applications for biological and chemical sensing. Most acoustic sensors are used for identification of biological targets, rather than measuring the response to environmental challenges such as antibiotic exposure. In this approach, it is thought that antibiotics cause nanoscale changes in the mechanical and electrical properties of bacteria, which can be detected using an acoustic sensor.

Here, we show that *E. coli* growth and adsorption is challenged by the antibiotic kanamycin when monitored using a shear-horizontal leaky surface acoustic (SH-LSAW) wave resonator. This effect occurs on a time-scale of about 30 to 60 minutes. The acoustic sensors were based on shear-horizontal leaky surface acoustic waves (SH-LSAW) propagating on 90° X rotated ST-quartz (ST-Q; 0°, 132.75°, 0°) and 36° Y-cut lithium tantalate (36YLT; 0°, −54°, 0°). Such methods can be useful for determining antibiotic susceptibility of bacterial samples more rapidly than conventional methods, e.g., in order to speed the appropriate therapy and increase the survival rate of infected patients.

The measurements were performed using a new monitoring approach for acoustic and radiofrequency (RF) sensors. Of significance is the development of an active shunt capacitance cancelling oscillator (ASCCO) for resonator parameter extraction. This oscillator removes the contribution of the shunt capacitance from the acoustic resonators, allowing precise tracking of the series resonance frequency and monitoring of only the acoustic contributions to be measured and tracked accurately. This monitoring method avoids impedance distortion and phase shift problems associated with non-zero shunt capacitance, and such a method can have wide, general applicability to acoustic sensors and RF devices. Additional details follow.

Example 2: Acoustic Resonators and Biosensor Applications

Over the past 30 years, the emergence of drug resistant bacteria is overwhelming our ability to develop new antibiotics fast enough. Consider from 1940 to 1962, more than 20 new classes of antibiotics were marketed; however, since then only two new classes have reached the market (see, e.g., Coates A R et al., "Novel classes of antibiotics or more of the same?," *Br. J. Pharmacol.* 2011; 163(1):184-94). Though antibiotic analogues have kept pace with the emergence of resistant bacteria until 10-20 years ago, not enough analogues have reached the market. Recently, only two new antibiotics have been discovered: fidaxomicin, a narrow spectrum macrocyclic for *C. difficile* infections; and teixobactin, a new class of antibiotics with broad activity against gram-positive bacteria. Despite these advances, a rapid approach is needed to slow the emergence of resistant bacteria (e.g., gram negative) and prevent the spread of resistant infections by using efficacious antibiotics at the onset of infection.

It is increasing important to determine antimicrobial susceptibility on a rapid timescale (e.g., minutes). In this approach, it is thought that antibiotics cause nanoscale changes in the mechanical and electrical properties of bacteria that can be detected using acoustic sensors. Moreover, if the bacteria are susceptible to the antibiotic, nanoscale changes begin to occur within minutes of exposure. This approach is based on a recent finding that a mechanical method such as atomic force microscopy (AFM) can rapidly characterize bacterial metabolism and quantitatively screen in five minutes their response to antibiotics by covalently attaching ~600 bacteria to cantilevers with no incubation period (see, e.g., Longo G et al., "Rapid detection of bacterial resistance to antibiotics using AFM cantilevers as nanomechanical sensors," *Nat. Nanotechnol.* 2013; 8(7): 522-6; and Soon R L et al., "Atomic force microscopy investigation of the morphology and topography of colistin-heteroresistant *Acinetobacter baumannii* strains as a function of growth phase and in response to colistin treatment," *Antimicrob. Agents Chemother.* 2009; 53(12):4979-86).

In addition, a purely electrical method, impedance spectroscopy, can detect changes in bacterial capacitance due to antibiotic challenges within 2 hours at concentrations as low as 80 cfu/ml (see, e.g., Sengupta S et al., "A micro-scale multi-frequency reactance measurement technique to detect bacterial growth at low bio-particle concentrations," *Lab Chip* 2006; 6(5):682-92; and Malleo D et al., "Continuous differential impedance spectroscopy of single cells," *Microfluid Nanofluidics* 2010; 9(2-3):191-8). These results suggest that detectable mechanical and electrical changes occur in bacterial cells during antibiotic exposure, which can enable much faster screening approaches than currently available.

Existing growth-based approaches currently require 12 hours to 21 days, especially for slow growing bacteria such as *mycobacterium*. Determining antimicrobial susceptibility is of paramount importance since all antibiotics approved for use in patients today are derived from a limited number of types, or classes, of antibiotics that were discovered by the mid-1980s.

Acoustic resonators are able to detect mechanical and electrical properties simultaneously with a mass detection limit in the sub femtogram range. The mass sensitivity depends on the acoustic mode and typically improves with increasing frequency. For a SH-LSAW based resonator with a passivation layer, the mass sensitivity $S_m^f$ is a function of the acoustic velocities, densities, and thicknesses of the layers (for a resonator including a piezoelectric substrate, an overlayer (e.g., a guide layer) disposed above the substrate, and a thin layer of mass disposed above the thin film, see, e.g., Wang Z et al., "Sensitivity analysis for Love mode acoustic gravimetric sensors," *Appl. Phys. Lett.* 1994; 64(22):2940-2; and Wang Z et al., "Perturbation method for analyzing mass sensitivity of planar multilayer acoustic sensors," *IEEE Trans. Ultrason. Ferroelect. Freq. Contr.* 1996; 43(5):844-51):

$$S_m^f = \frac{1}{f_0} \lim_{\Delta m \to 0} \left[ \frac{f - f_0}{\Delta m} \right] \approx \frac{1}{f_0} \frac{\partial f}{\partial m} = -\frac{\left(1 - \frac{V_{S_3}^2}{V_0^2}\right)}{\rho_2 h \cdot \left[1 + \frac{\sin(\beta_2 h)\cos(\beta_2 h)}{\beta_2 h} + \frac{\rho_1}{\rho_2} \cdot \frac{\cos^2(\beta_2 h)}{\beta_1 h}\right]}, \quad (1)$$

where f is the oscillation frequency at perturbed cases, $f_0$ is the frequency at unperturbed cases, $\Delta m$ is the perturbation of change in mass, $V_0$ is the phase velocity of the acoustic mode at unperturbed cases, $V_{S_3}$ is the shear wave velocity in the thin layer of mass, $\rho_1$ is the density of the semi-infinite piezoelectric substrate, $\beta_2$ is the decay constant in the substrate, $\rho_2$ is the density of a thin overlayer, h is the height of the overlayer, and $\beta_2$ is the transverse propagation constant in the overlayer.

To improve mass sensitivity, the sensors are often designed to have an operating frequency in the MHz to GHz range; however, there are practical limits on the operating frequency due to photolithography, complexities of the monitoring circuit, electrical and acoustic losses, and associated parasitic contributions. For perspective, one bacterium has a mass of one picogram and one virus has a mass of one femtogram, thus achieving high mass sensitivity is paramount.

In this study, 1-port shear-horizontal leaky surface acoustic wave (SH-LSAW) resonator was designed in ST-Quartz at 100 MHz to enable the development of a method to remove the shunt capacitance from the resonators. ST-Quartz was chosen for its high quality factor (Q) and low temperature dependence to prototype the active shunt capacitance cancelling oscillator (ASCCO).

The SH-LSAW resonators were fabricated on ST-Quartz (0°, 132.75°, 0°) and also on 36° Y-cut lithium tantalate (36YLT) (0°, −54°, 0°) to access the SH-LSAW mode. The SH-LSAW mode was excited by depositing a thick metal layer with a high density such as tungsten, gold, or tantalum (see, e.g., Kadota M et al., "Resonator filters using shear horizontal-type leaky surface acoustic wave consisting of heavy-metal electrode and quartz substrate," *IEEE Trans. Ultrason. Ferroelect. Freq. Contr.* 2004; 51(2):202-10). For ST-Quartz, the SH-LSAW mode propagates at a 90° rotation to the axis (ST-90° X) with an electromechanical coupling ($K^2$) factor of 0.4%. The energy of the LSAW mode is concentrated in the structure due to the dense electrodes, allowing a very compact layout compared to conventional Rayleigh-mode resonators. In addition, a very weak Rayleigh wave is produced when propagating along the X-axis (ST-X, $K^2$=0.12%) in ST-Quartz. The acoustic velocity of the SH wave is 5100 m/s and the Rayleigh wave is 3400 m/s at the ST-90° X rotation. Thus, these modes are separated in frequency by a factor of 1.5× in ST-Quartz.

For 36YLT, acoustic propagation was parallel to the X-axis. The SH-LSAW velocity is 4077 m/s with a $K^2$=5.4%. A weak Rayleigh mode is also excited in 36YLT, which propagates at a 90° rotation to the X-axis (0°, −54°, 90°) with a velocity of 3152 m/s and $K^2$=0.035%. These acoustic modes are separated in frequency by a factor of 1.3× in 36YLT. The Rayleigh mode is very weak and the interdigital transducer (IDT) does not excite an acoustic wave, thus only a capacitor is formed by the IDT. The SH-LSAW resonators were designed to target a series resistance ~50Ω.

For both substrates, the R modes are very weak Rayleigh waves that appear out-of-band from the series resonance frequency. These modes serve as a reference (R) or inactive resonator, which are used to remove the shunt capacitance ($C_o$) for the Active Shunt Capacitance Cancelling Oscillator (ASCCO).

Example 3: SH-LSAW Resonator with an Inactive Resonator as the Reference Capacitor Acoustic resonators were fabricated to utilize the propagation of SH-LSAW waves. To minimize resistive losses when using the monitoring circuit, the series resistance of the resonator was designed to be about 50Ω. If this resistance is too low (e.g., less than about 10Ω), then the sensor appears as an electrical short to the monitoring circuit, which prevents start-up of the oscillator. If the series resistance is too high (e.g., more than about 300Ω), the loop gain of the detection will be too high and cause excessive noise. The IDTs were fabricated using 5000 Å tungsten (W) or gold (Au) with a 100 Å Ti adhesion film to provide high acoustic reflectivity per finger pair.

Figure 2A:
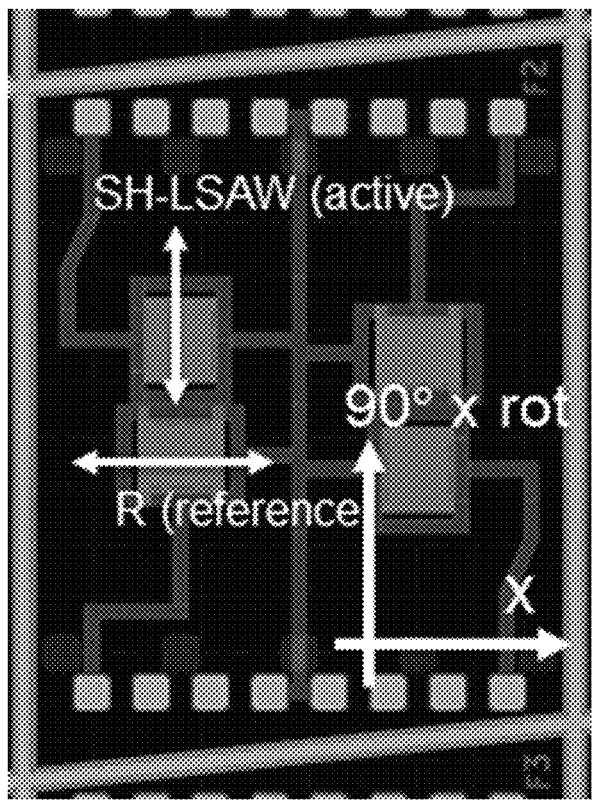
FIGS. 2A-2B show fabricated active and inactive sensors. Provided are (A) images of a fabricated SH-SAW sensor (active sensor) and a reference capacitor (inactive sensor). Propagation along the 90° rotation to the X-axis produces SH-LSAW (active sensor), where propagation along X-axis produces an inactive sensor for removal of the shunt capacitance. Also provided is (B) a micrograph of the fabricated sensor with 25 finger pairs. The tungsten thickness was 0.5 μm. A film of 1000 Å $SiO_2$ was deposited over the sensors. There are 10 Bragg reflector strips, and BL indicates bussing lines. Overall, the device measures 1.8 mm×2.4 mm.
Figure 2B:
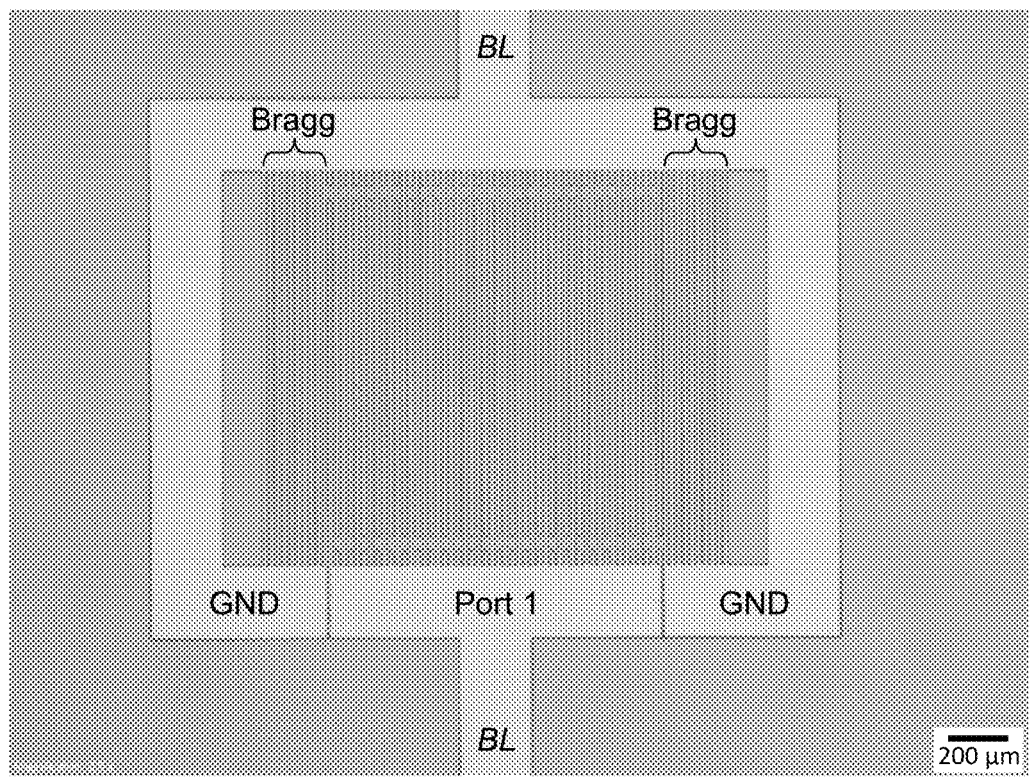

The wavelength of the ST-90° X devices was 46 µm, giving a resonator frequency of 100 MHz (FIG. 2B). The finger width was 11.5 µm with an aperture of 25λ and 25 finger pairs. For the 100 MHz 36YLT resonators, the wavelength was 38 µm, with a finger width of 9.5 µm, an aperture of 25λ, and 25 finger pairs. The sensors had 500 Å to 1000 Å of $SiO_2$ deposited to passivate the IDTs.

In FIG. 2A, the layout is shown for the piezoelectrically active (working) resonator and the inactive resonator, which functions as a reference capacitor (R). The purpose of the inactive channel is to remove the effect of the non-zero shunt capacitance ($C_o$) in parallel with the motional resistance ($R_m$), motional inductance ($L_m$), and motional capacitance ($C_m$) of the sensor. It is desirable to measure the mechanical and electrical contributions of the acoustic resonators to avoid impedance distortion and phase shift problems associated with non-zero shunt capacitance. Thus, removing the shunt capacitance is highly desirable.

Shunt capacitance removal was achieved by using an inactive sensor that had no piezoelectric mode in the same frequency range as the active channel. The approach required creating the same shunt capacitance as the working sensor without piezoelectric activity. In general, for a SAW sensor, this is accomplished by fabricating an identical IDT that propagates an out-of-band or weakly coupled mode (e.g., a Rayleigh mode). For a bulk acoustic wave (BAW) sensor, this can be achieved by forming the equivalent shunt capacitance using an out-of-band acoustic mode (e.g., a Rayleigh mode) or fabricating a capacitor in proximity to the working sensors to obtain similar temperature dependence.

Example 4: Electrical Response of Resonators

Figure 3A:
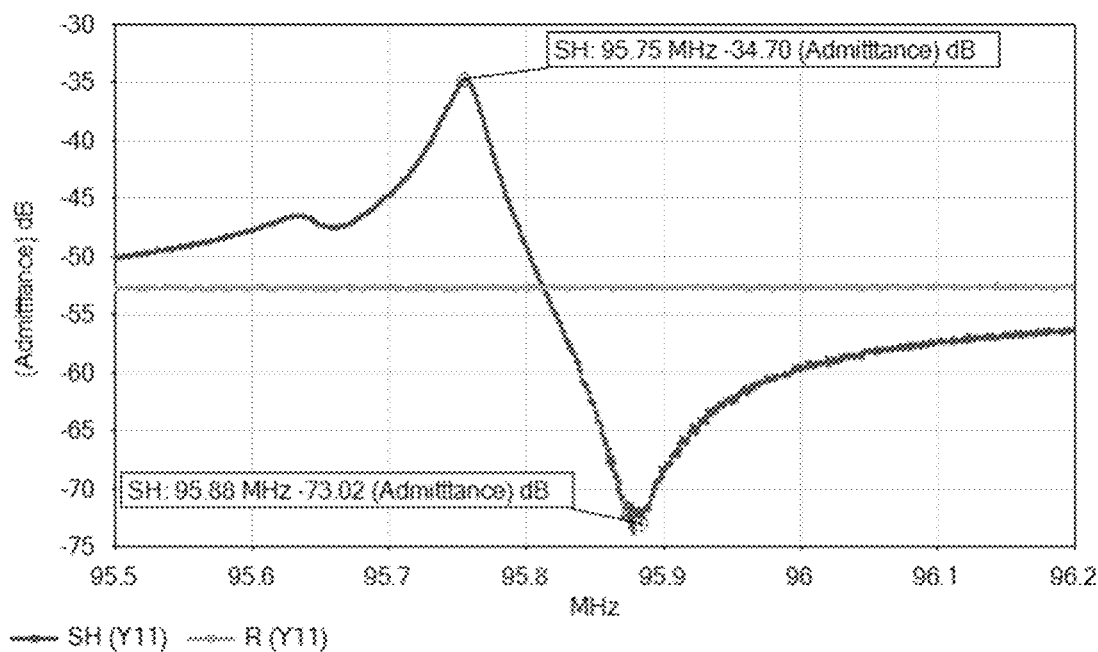
FIGS. 3A-3B show measured admittance of ST-90° X (magnitude and phase) of SH mode device (dark gray) and the reference (R) device (light gray) in air.
Figure 3B:
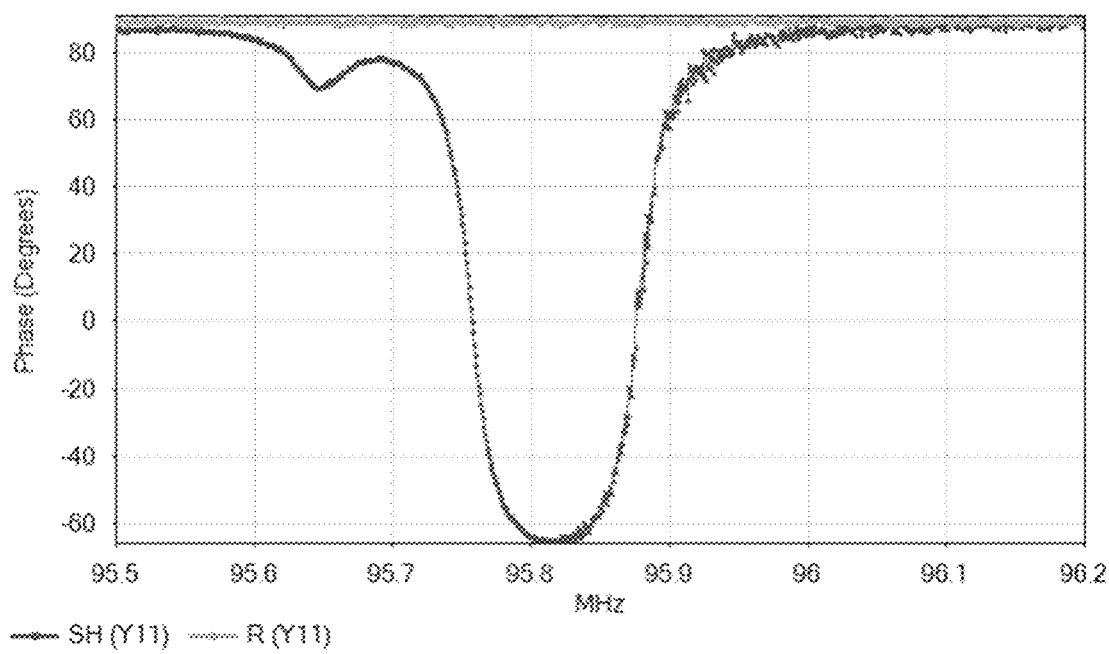

The electrical response of the ST-Quartz SH-LSAW sensors was measured on a probe station and is shown in FIGS. 3A-3B for air. The response confirms the presence of an SH-LSAW propagating mode with a frequency of 95 MHz. A Levenberg-Marquardt nonlinear fit was performed using the expression for the admittance of a 1-port resonator (see, e.g., Bandey H L et al., "Modeling the responses of thickness-shear mode resonators under various loading conditions," *Anal. Chem.* 1999; 71(11):2205-14):

$$SSE(f(C_0, R_m, F_s)) = \sum \text{residuals}(f(C_0, R_m, F_s))^2 = 0 \quad (2)$$

$$Y_u = j\omega C_o + \frac{1}{R_m\left(\frac{\omega}{\omega_s}\right)^2 + j\omega\left[\frac{(N\pi)^2}{8K^2 C_o}\left(\frac{1}{\omega_s^2}\right) - \frac{1}{\omega^2}\right]} = j\omega C_o + \frac{1}{R_m + j\omega L_m + \frac{1}{j\omega C_m}}$$

$$C_m = \frac{8K^2 C_o}{\pi^2}$$

$$L_m = \frac{1}{\omega_s^2 C_m}$$

$$\omega_s = 2\pi F_s$$

where $\omega_s$ is the angular series resonance frequency, $F_s$ is the series resonance frequency, N is the harmonic mode, $K^2$ is the electromechanical coupling constant, $C_o$ is the static or shunt capacitance, ω is the angular frequency, $R_m$ is the dissipation in the system, $L_m$ is the inertial mass, and $C_m$ is the mechanical elasticity of the system. The fitted values were as follows: $F_s$=95.7 MHz, $K^2$=0.31%, $C_o$=3.6 pF, $C_m$=8.9 fF, $L_m$=309 µH, $R_m$=54Ω, and the quality factor Q=3412. This device has an excellent Q with a weak electromechanical coupling constant. A fit to the inactive reference capacitor ($Z=j\Omega C_o$) gave $C_{o,ref}$=3.88 pF. This is very close to the shunt capacitance of the active resonator. These resonators were used to develop the ASCCO measurement hardware.

Figure 4A:
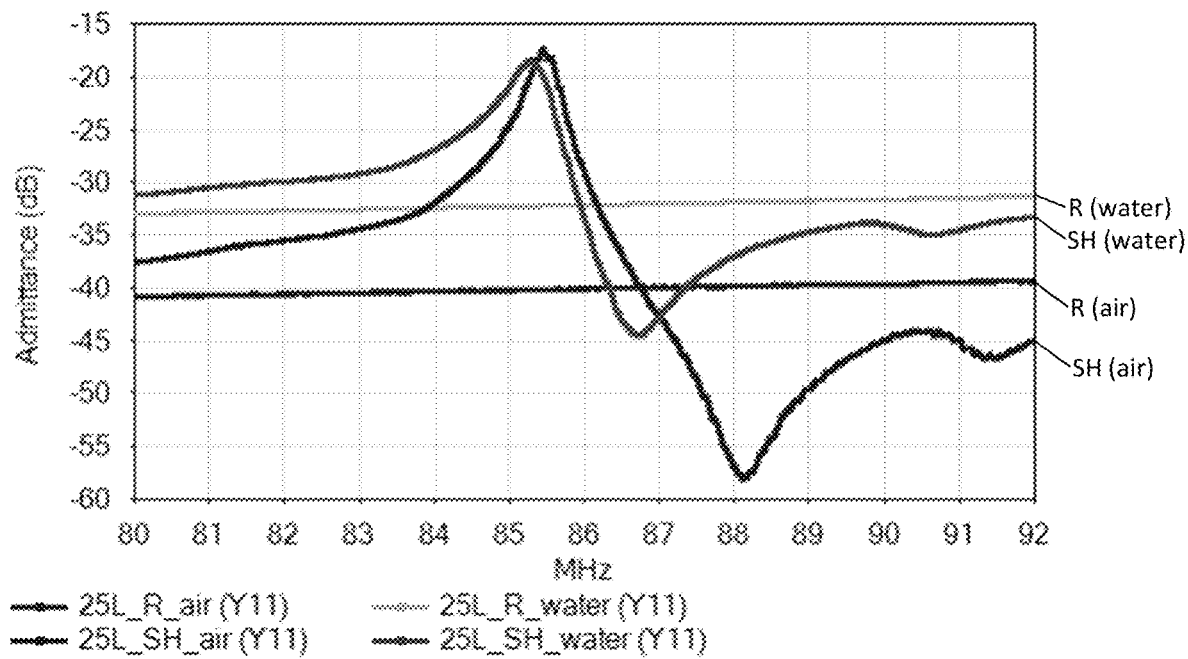
FIGS. 4A-4B show measured admittance of 36YLT (magnitude and phase) of SH mode device (labeled "SH") and the reference (R) device (labeled "R") in air and water. Devices were fabricated with Au IDTs.
Figure 4B:
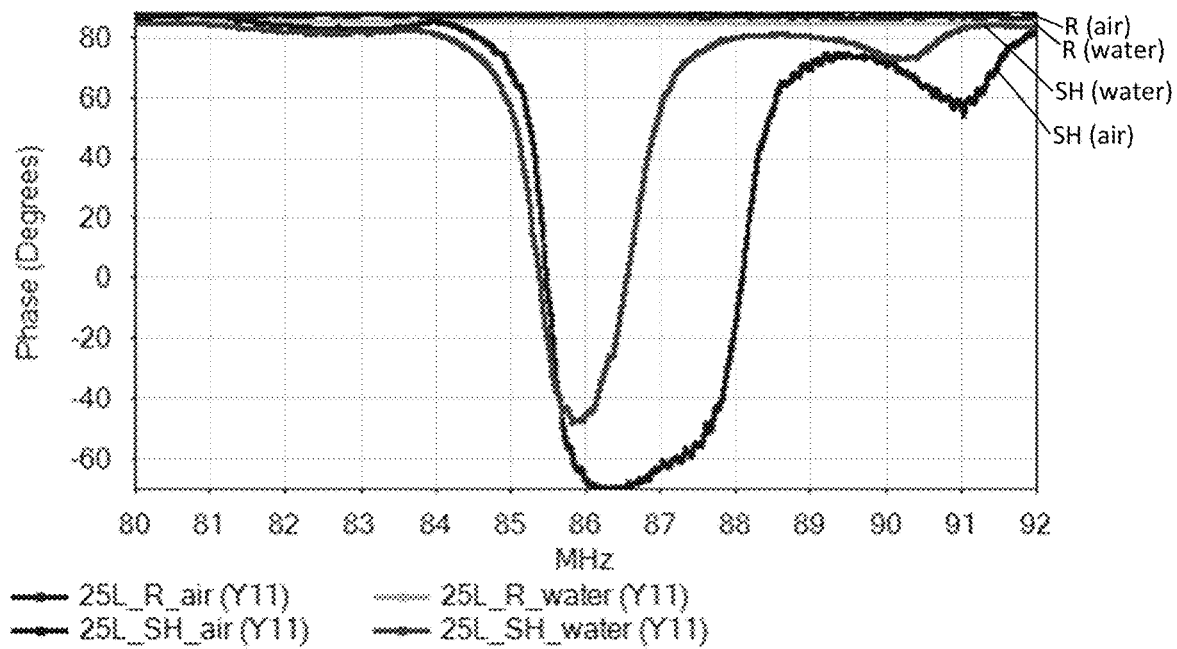

In FIGS. 4A-4B, the admittance and phase responses are shown for the 36YLT resonators. The resonance frequency was ~ 85 MHz, since the same design was used for this substrate and cut; however, this did not impact the measurement approach. The fitted values for air were as follows: $F_s$=85.5 MHz, $K^2$=7.2%, $C_o$=17.8 pF, $C_m$=1.0 pF, $L_m$=3.3 µH, $R_m$=7.2Ω, and Q=254. A fit to the inactive reference capacitor ($Z=j\Omega C_o$) in air gave $C_{o,ref}$=18.4 pF. The fitted values for water were as follows: $F_s$=85.3 MHz, $K^2$=4.0%, $C_o$=43.2 pF, $C_m$=1.4 pF, $L_m$=2.5 µH, $R_m$=8Ω, and Q=165. The Q for this type of resonator is much lower than ST-90° X in air, but ST-90° X cannot operate when loaded with water due to its small $K^2$. A fit to the inactive reference capacitor ($Z=j\omega Co$) in water gave $C_{o,ref}$=46.0 pF. These 36YLT sensors were not optimized and higher Qs are possible by reducing the number of excitation fingers in the IDT. Reducing the number of finger pairs would increase the Q while reducing the electromechanical coupling constant. Further optimization of the Bragg reflectors could improve the performance; however, the sensors were suitable for measurements in water.

Example 5: Impact of Shunt Capacitance

The equivalent circuit of a 1-port acoustic resonator ($Y_1$) is shown in FIG. 5. $C_o$ is the shunt capacitance, $R_m$ is the motional resistance, $L_m$ is the motional inductance, and $C_m$ is the motional capacitance. This motional arm of the resonator is due to the piezoelectric characteristics of the resonator.

Figure 6A:
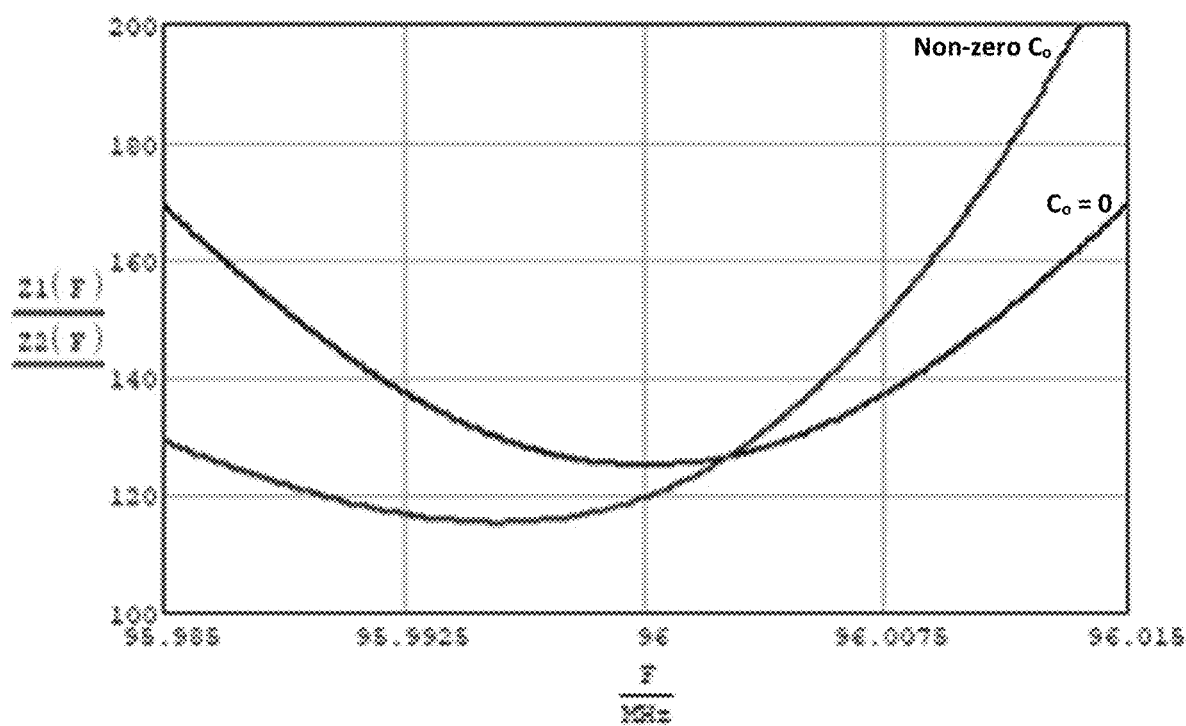
FIGS. 6A-6B show the impact of shunt capacitance ($C_o$) on the resonator. Provided are graphs showing (A) resonator impedance as a function of frequency for non-zero $C_o$($C_o$=4 pF) and $C_o$=0 and (B) resonator impedance phase as a function of frequency for non-zero $C_o$($C_o$=4 pF) and $C_o$=0.
Figure 6B:
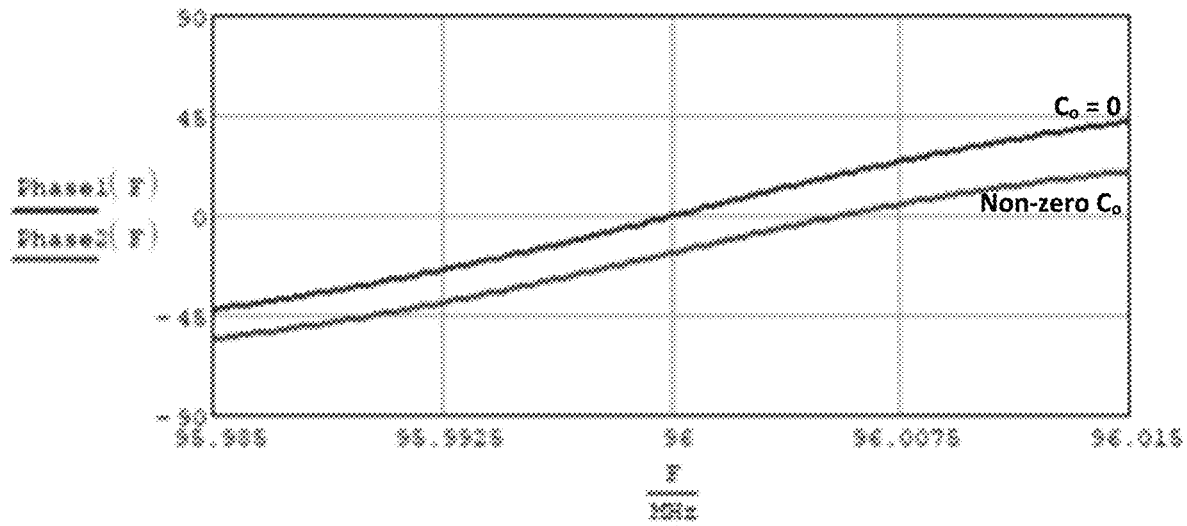

Non-zero shunt capacitance alters the impedance by shifting the location of the minimum and the zero phase crossing while causing significant distortion. In some cases, there may not be a zero phase crossing (FIGS. 6A-6B). The distortion for non-zero shunt capacitance becomes increasingly worse as the resonator loss increases (i.e., low Q). The shunt capacitance $C_o$ is always a non-zero value, due to the electrodes and the additional capacitance of the associated fixture or circuit substrate used for the sensor.

To obtain the true $F_s$ and resonator loss $R_m$, it is highly desirable to remove the shunt capacitance because more useful information can be generated by an oscillator or other measuring equipment. When $C_o$=0, the series resonance occurs exactly where the phase crosses zero at the minimum impedance or series resonance. This is because the resonance is now due to the combination of $L_m$-$C_m$, and $Y_1$ appears as $R_m$ at the series resonance frequency $F_s$ when is $C_o$ is a very large reactance compared to $R_m$. At $F_s$, the sensor is most sensitive to surface changes. Resonator-sensor applications require monitoring $F_s$ and $R_m$, as this provides information relating to mass change ($\Delta m$) and viscosity-density of the measured sample ($R_m$ or Q). It is important to note that the location of $F_s$ for $C_o$=0 may differ from the location of the quality factor Q due to the phase shift contribution from $C_o$:

$$Q_s = \frac{F_s}{2} \frac{d\angle Z_{11}}{df} = \frac{2\pi F_s L_m}{R_m}, \quad (3)$$

where $Z_{11}$ is the 1-port impedance, $F_s$ is the series resonance frequency, $R_m$ is the motional resistance, and $L_m$ is the motional inductance. Equivalently, Q can be computed from $L_m$ and $R_m$.

Example 6: Exemplary Active Shunt Capacitance Cancelling Oscillator (ASCCO)

An oscillator circuit was developed to remove the impedance contribution of $C_o$, allowing the acoustic contributions to be measured by the oscillator. This method is called Active Shunt Capacitance Cancelling Oscillator (ASCCO). The oscillator tracks the true resonant frequency $F_s$ and thus provides the best sensitivity to surface changes, such as mass and viscosity density, which can be critical for sensor applications.

When $C_o$ is removed, a series resonant oscillator circuit is formed that "servos" the zero-phase point of this effective resonator impedance, which is determined the motional arm of the resonator structure. The zero impedance phase of this motional arm occurs at the $F_s$ of the resonator, where the shunt capacitance complicates finding the "true" $F_s$ of a resonator since this frequency depends on this shunt capacitance and the resonator loss, $R_m$.

Extracting the value of $R_m$ from a series resonant oscillator that removes the shunt capacitance at series resonance simplifies the resonator impedance to $R_m$. This does not require deconvolving the shunt capacitance. The active shunt capacitance cancelling oscillator allows the above conditions by removing any shunt capacitance across the resonator. Removal is accomplished by supplying the circuit with an equal "dummy" capacitance that generates a cancelling current used in the oscillator to cancel electronically the non-desired resonator shunt capacitance. This circuit also supplies an output signal (e.g., a dc voltage) that is proportional to the amplitude of oscillation which is also proportional to $R_m$. At the series resonance frequency $F_S$ of $L_m$-$C_m$, only $R_m$ remains and $C_o$=0 or $C_o$ is a very large reactance compared to $R_m$.

Figure 8A:
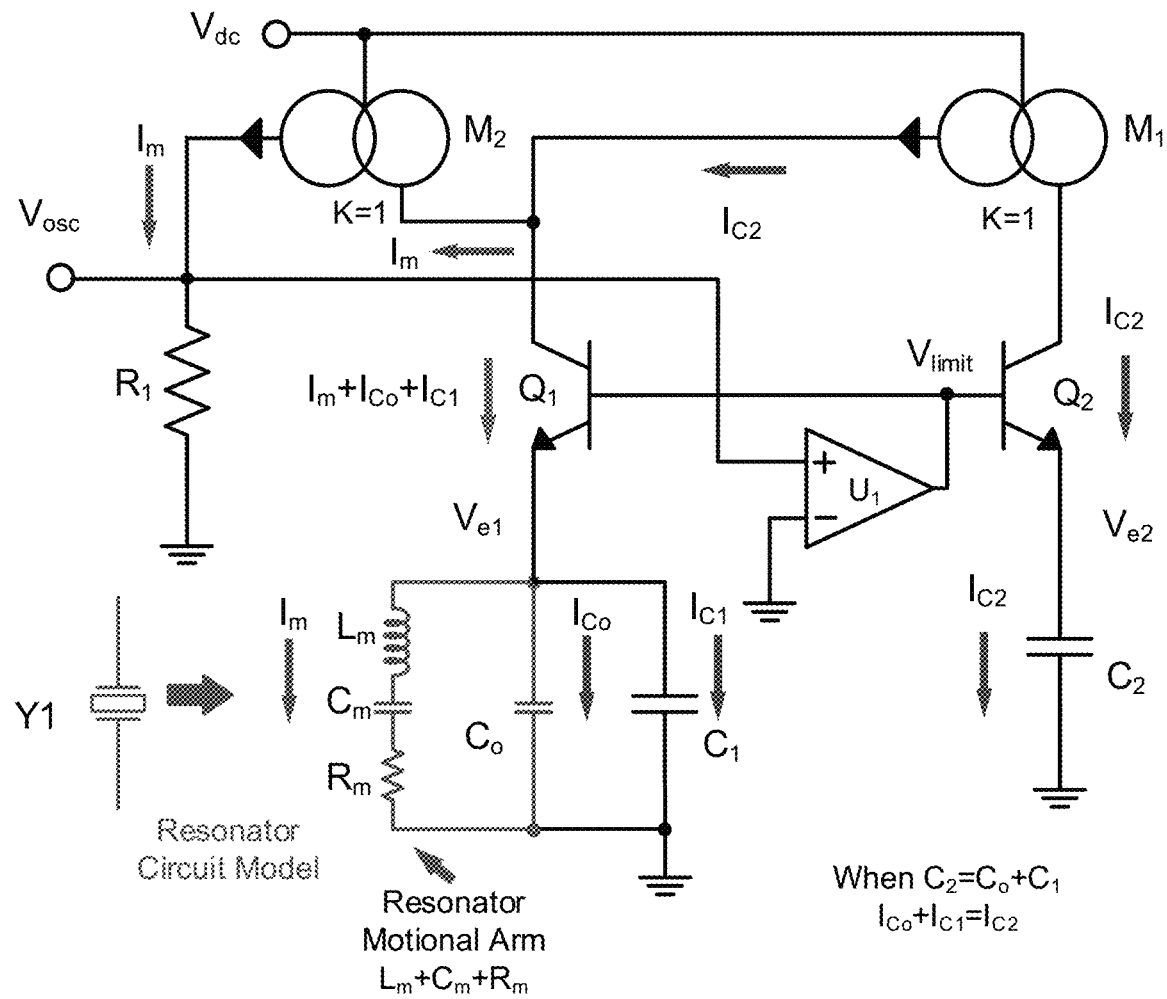
FIGS. 8A-8B show (A) another exemplary oscillator circuit and (B) a simplified oscillator with active shunt $C_o$ removal.
Figure 8B:
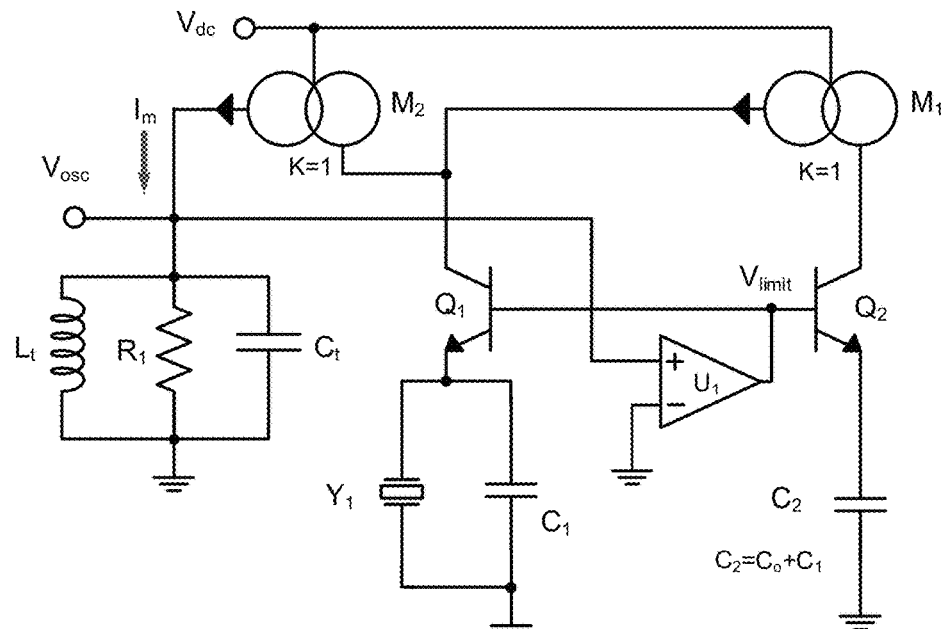

An exemplary circuit is shown in FIG. 8A. This oscillator uses the emitters of $Q_1$ and $Q_2$ as active ports to convert impedances of the resonator with shunt capacitance $C_1$ (emitter of $Q_1$) and a dummy capacitance $C_2$ (emitter of $Q_2$) into currents that will be summed at an output node. In this way, the equivalent circuit functions as an oscillator, where the frequency of oscillation only depends on the motional arm of the resonator circuit. This is true when the output impedance of $Q_1$ and $Q_2$ are less than the impedances at these nodes, or the transistors are working as very good voltage followers, meaning the emitter voltages, $V_{e1}$ and $V_{e2}$ are very close to the output voltage of the limiting amplifier $U_1$.

In one non-limiting instance, the limiting amplifier is a non-inverting amplifier with gain ($GU_1$) of approximately 2.25, and the output is fixed to limit to an amplitude a predetermined voltage (e.g., about 0.4 Vp-p). This voltage is independent of the input amplitude ($V_{osc}$) after this level is reached. To cancel the effects of the shunt capacitance across the resonator ($C_o$+$C_1$), the value of $C_2$ needs to equal $C_o$+$C_1$. As shown in FIG. 8A, the current mirror $M_1$ passes on a copy of the dummy capacitance current $I_{C2}$ to current mirror $M_2$, where the summing of the two current legs $Q_1$ and $Q_2$ cancel the shunt capacitance currents ($I_{Co}$, $I_{c1}$, $I_{C2}$) and leaves only the motional arm current $I_m$.

The resulting motional arm current $I_m$ generates an output signal (e.g., voltage $V_{osc}$ at node $R_1$). Resistance $R_1$ is real and equal to 340Ω, and the gain of $U_1$ is also real. Thus, the loop gain $A_v$ is $R_1(GU_1)/(XL_m+XC_m+R_m)$, where $XL_m$ and $XC_m$ are the reactance of $L_m$ and $C_m$, respectively. The circuit will oscillate when the loop gain is greater than one and the oscillation frequency occurs where the loop function is real, or $2\pi$ radians. This condition only occurs when $XC_m+XL_m$=0 or when $F_{osc}$=$1/(2\pi\sqrt{(L_mC_m)})$. The loop gain equation at this frequency is $R_1(GU_1)/R_m$. The voltage at node $V_{osc}$ is simply the limiting voltage of $U_1$ (e.g., 0.4Vp-p) multiplied by the ratio ($R_1/R_m$). In reality, the resistor $R_1$, which can be relatively large, is shunted with capacitance also. Thus, in practice, at the node $V_{osc}$, $R_1$ uses a parallel tank circuit to allow a wider possible range of operational frequencies and/or selection of a resonator overtone, if desired.

In FIG. 8B, a simplified version of an exemplary active capacitance canceling oscillator is shown. The output tank, at $V_{osc}$, is a parallel tank circuit where $R_1$, $L_t$-$C_t$ is a relatively low Q parallel tank circuit, where $L_t$ is chosen to be resonant with $C_t$ at the desired resonator frequency. At this frequency, the tank impedance is simply $R_1$, and the previous equations and theory all apply. The amplitude of the oscillation is taken from a node inside $U_1$, which provides a half wave rectification of the node $V_{osc}$. This signal can range from a low to high-level sine wave, depending on the resonator loss and other parameters. The rectified waveform can be buffered and filtered to provide an output signal (e.g., a dc voltage) proportional to the amplitude of the oscillation voltage at $V_{osc}$. In one non-limiting instance, the oscillator operates with a series resistance of from about 10Ω to about 250Ω. In other non-limiting instances, above about 300Ω, the oscillate may fail to operate due to a decrease in the overall loop gain of the detection circuit.

To confirm the ASCCO circuit is removing the shunt capacitance and tracking the true series resonance, capacitance was added to the active and dummy oscillator ports in sequence. Adding a 2.5 pF capacitor to the active resonator port caused an equal but opposite frequency shift +30 ppm. Adding a 2.5 pF capacitor to the dummy or reference resonator port caused an equal but opposite frequency shift of −49 ppm. Both ports had an expected but small decrease in amplitude. Adding equal capacitors to both oscillator ports resulted in a negligible shift in the oscillator frequency of 2 ppm and the oscillator amplitude remained unchanged. This shows the ASSCO circuit is tracking the true series resonance frequency.

Example 7: Fluidic Module for Use with an Acoustic Resonator

Figure 10A:
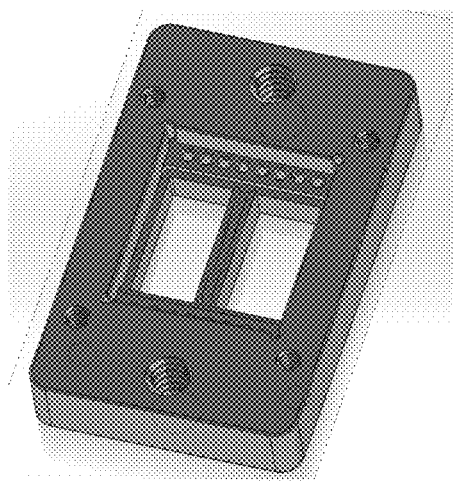
FIGS. 10A-10C show an exemplary fluidic module. Provided are (A) a SolidWorks Model of a fluidic cell; (B) a 3D printed fluidic package; and (C) a photograph of a 3D printed fluidic cell including RF connectors and a gasket.
Figure 10B:
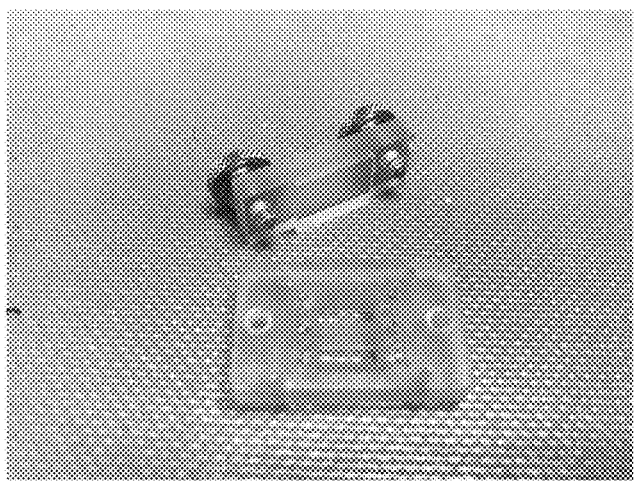
Figure 10C:
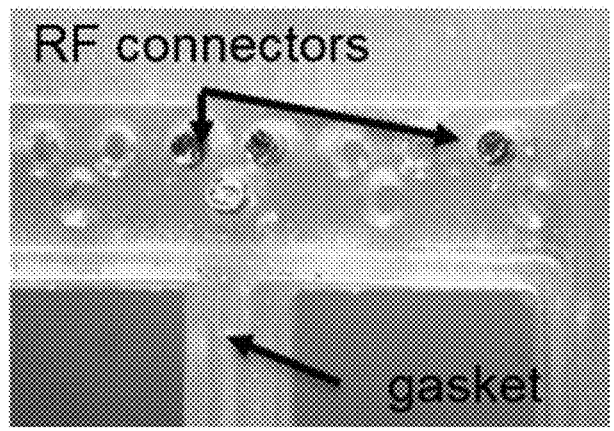

To confine a sample (e.g., a biological buffer) on the SH-LSAW resonators, a fluidic cell was printed from an acrylate polymer using a digital light processing (DLP) MIICraft 125 Series—50 Printer (MIICraft, Taiwan) (FIGS. 10A-10B). The XY resolution was 30 μm, and the Z resolution was 5 μm. The RF connectors (e.g., fuzz buttons) were 100 mil length and 20 mil in diameter (Custom Interconnects, Centennial, CO). Each fuzz button was inserted into the through holes in the 3D printed fixture (FIG. 10C).

Figure 11:
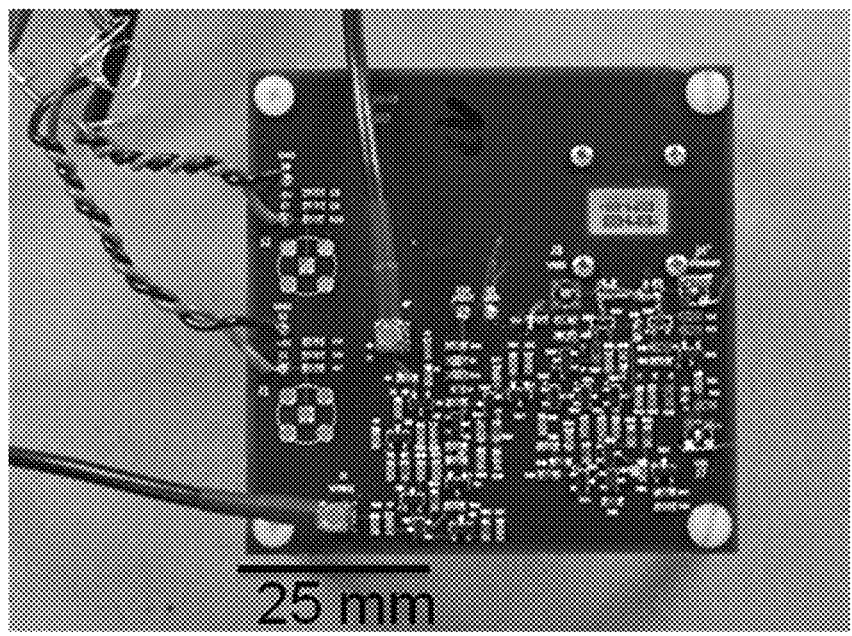
FIG. 11 shows an exemplary printed circuit board with a fluidic module including a microfluidic cell.
Figure 12:
FIG. 12 shows oscilloscope measurements for an exemplary single-port ST-90° rotated X-cut quartz resonator/sensor oscillator ($F_s$=96 MHz).
Figure 13A:
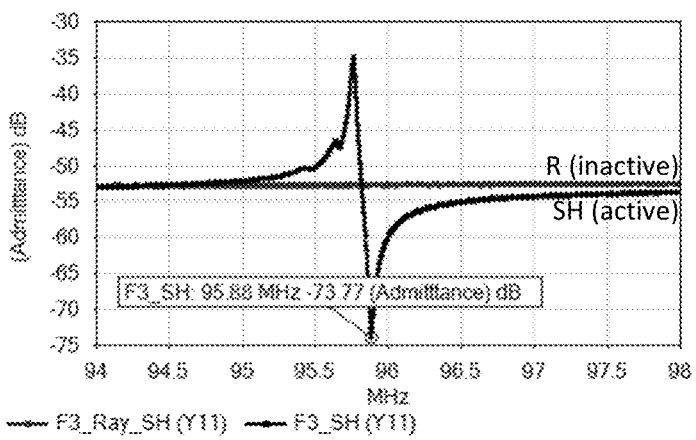
FIGS. 13A-13B show performance for a ST-quartz sensor (0,132.75,0) propagating at a 90° rotation to the x-axis (90° x rot.). Provided are (A) admittance and (B) phase responses for the pure shear horizontal (SH, $F_s$ of 95.7 MHz, Q of 3412, $K^2$ of 0.31%, $C_o$ of 3.5 pF, $L_m$ of 309 μH, $C_m$ of 8.9 fF, $R_m$ of 54Ω, TCF ~0 ppm/° C.) and reference (R) modes, in which the R mode is not acoustically active and serves as a reference capacitor.
Figure 13B:
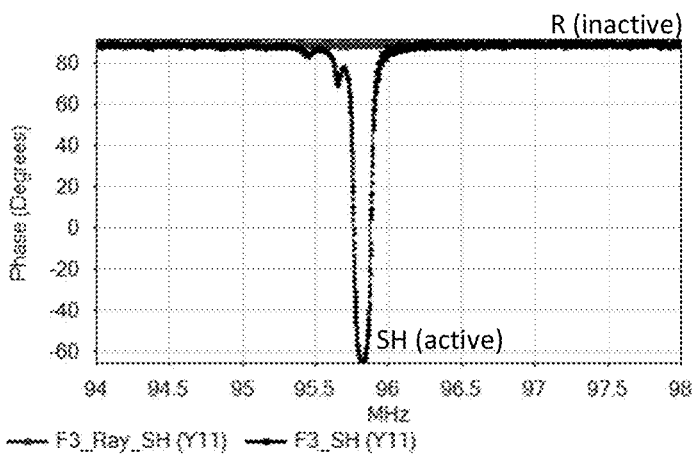

The oscillator circuit was provided as a printed circuit board (FIG. 11), to which the fluidic module was mounted. The measured waveforms corresponded to the resonator, input of the limiting amplifier, output of the limiting amplifier, and the reference capacitor or dummy (FIG. 12). FIGS. 13A-13B provides sensor performance for a ST-quartz resonator (active resonator) and an inactive resonator (reference) operating in pure shear horizontal mode.

Example 8: Biological Assays Employing Acoustic Resonators

Any useful biological assays can be conducted employing the systems herein. In one instance, the assay includes determining whether a certain compound (e.g., an antibiotic) can be used to treat a particular cellular colony (e.g., bacterial cell colony). For instance, if the bacteria is susceptible to treatment with the compound, then bacterial growth may be slower, as compared to a control. Such a change in growth rate can be determined by employing an acoustic resonator, which can detect whether there is a change in bacterial mass (e.g., increased or decreased colony growth) or release of cells (e.g., release of lysed cells) at or from the resonator surface.

Figure 14A:
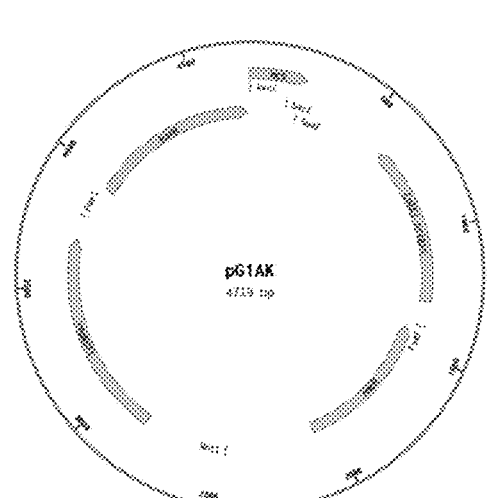
FIGS. 14A-14B show vector maps for *E. coli* DH5a bearing (A) pG1AK, an ampicillin and kanamycin (Amp+ Kan) resistance plasmid or (B) pACYC-LIC+, a chloramphenicol resistance plasmid.
Figure 14B:
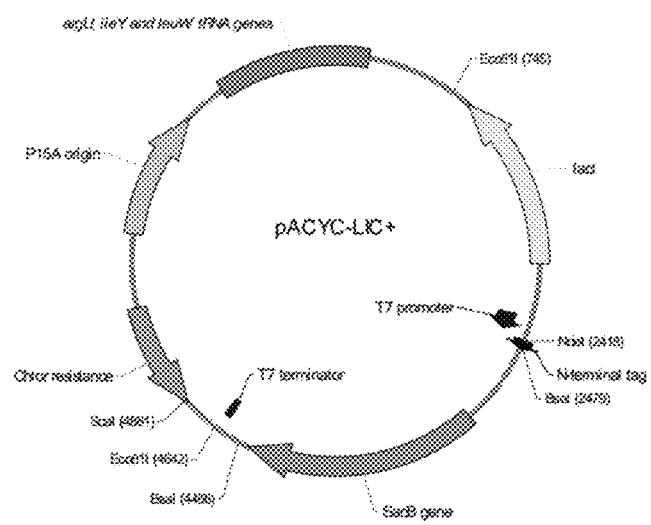

Assays were performed with TOP10 and DH5α strains of *E. coli*, which were purchased from Invitrogen and New England Biolabs respectively. *E. coli* MG1655 was purchased from ATCC. Plasmids pACYC-Lic+(chloramphenicol resistance) and PG1AK (kanamycin and ampicillin resistance) (FIGS. 14A-14B) were purchased from Addgene. All bacteria were cultured in LB medium at 37° C. with shaking.

For the SH-LSAW sensors to monitor physical properties of the bacteria being tested, the cells must be tightly coupled to the sensor surface. Although bacteria can adhere to $SiO_2$, silanization was tested to determine if it would improve the capture efficiency or strength of binding. In brief, borosilicate glass coverslips (Corning) were treated with 3-aminopropyl trimethoxysilane (APTMS). Coverslips were cleaned successively with acetone, methanol, 2-propanol, and water; dried with nitrogen; and then treated with UV-ozone for 15 minutes. Coverslips were then immersed in 1% APTMS in toluene for 15 minutes at room temperature, rinsed with toluene, then baked at 100° C. for 30 minutes.

*E. coli* cells grown to early stationary phase were labeled with 10 μM Syto®13 (nucleic acid probe) in Tris-buffered saline for 15 minutes, then resuspended at approximately $10^7$ cells/ml, and allowed to settle on coverslips for 15 minutes. Coverslips were then washed 3 times by dipping in Tris-buffered saline and mounted directly on slides for imaging (Olympus IX71 fluorescence microscope, 60× oil immersion objective).

Figure 15A:
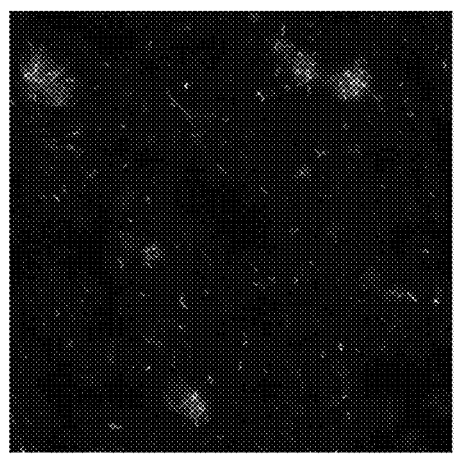
FIGS. 15A-15B show binding of bacterial cells on varying surfaces. Provided are fluorescence images of *E. coli* stained with Syto®13 and allowed to settle for 15 minutes on (A) 3-aminopropyl trimethoxysilane (APTMS)-treated glass coverslips or (B) untreated glass coverslips. After three washes in Tris-buffered saline, coverslips were mounted and imaged by fluorescence microscopy.
Figure 15B:
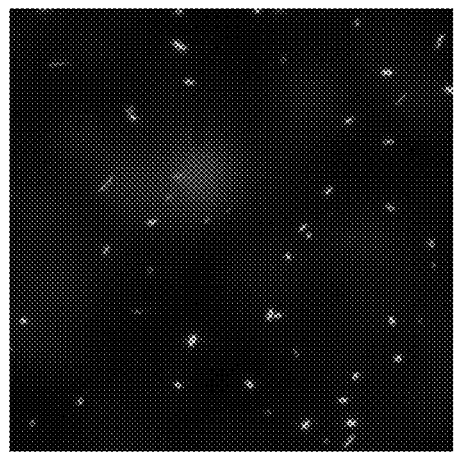

FIGS. 15A-15B show fluorescence microscopy of labeled *E. coli* bacterial cells on either bare borosilicate glass coverslips or the same surface treated with 3-aminopropyl trimethoxysilane. As expected, some bacteria adhered to the glass alone; however, silane treatment increased the number of bacteria still bound after washing coverslips with buffer, indicating stronger binding to the surface.

To perform an initial test of the sensors' ability to detect response of bacteria to antibiotics, common molecular cloning strains and one pseudo-wild-type strain of *E. coli* were selected. TOP10, DH5α, and MG1655 strains are sensitive to kanamycin, ampicillin, or chloramphenicol in the absence of a plasmid conferring resistance. Dose response growth curve analysis was performed to determine appropriate concentrations of antibiotic to use with each strain and plasmid combination.

To assess antibiotic dose response, each strain with each plasmid was cultured in 200 μL LB in 96-well microtiter plates for 24 hours in a Synergy H4 plate (BioTek Instruments, Inc., Winooski, VT) reader at 37° C. with 30 seconds shaking and collecting measurements of optical density at 600 nm (OD600) every 10-15 minutes. For experiments in which bacteria were applied to the resonator devices, cultures were harvested at late log to early stationary phase. Cells were centrifuged at 5000× g for 5 minutes then resuspended in either fresh LB medium or phosphate-buffered saline. For antibiotic treatment, 200 pg/ml kanamycin was added to cells in the sensor devices. Positive controls for cell death were conducted by adding sodium hydroxide to cells in the devices at a final concentration of 1M.

Figure 16A:
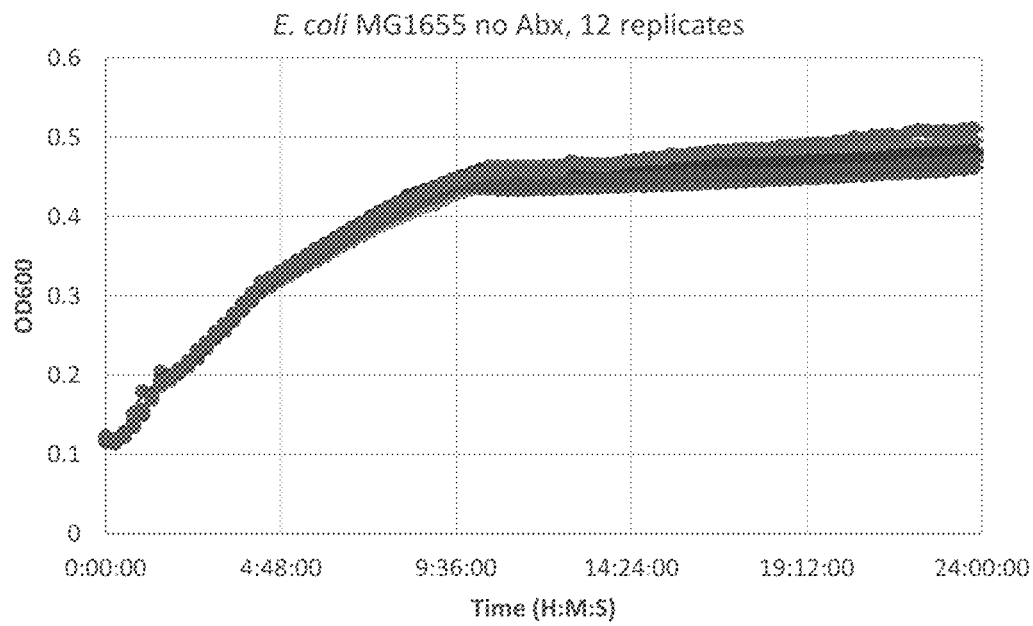
FIGS. 16A-16B show growth curve analysis of *E. coli* MG1655 cultures having (A) no exposure to antibiotics and (B) exposure to varying doses of ampicillin, as measured by optical density at 600 nm (OD600). Growth inhibition was observed at more than about 1.56 μg/mL.
Figure 16B:
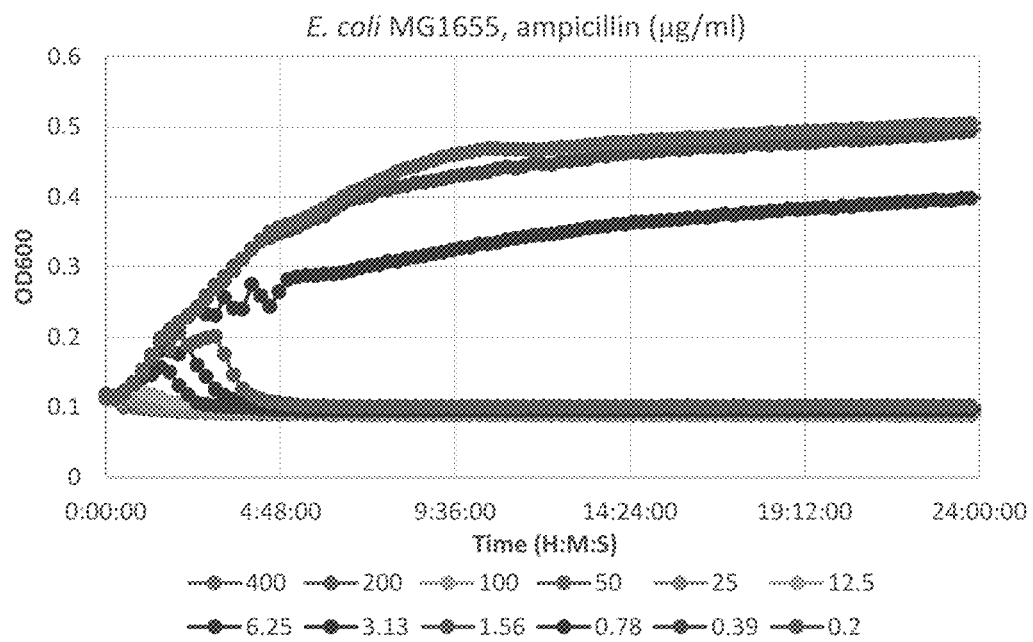
Figure 17:
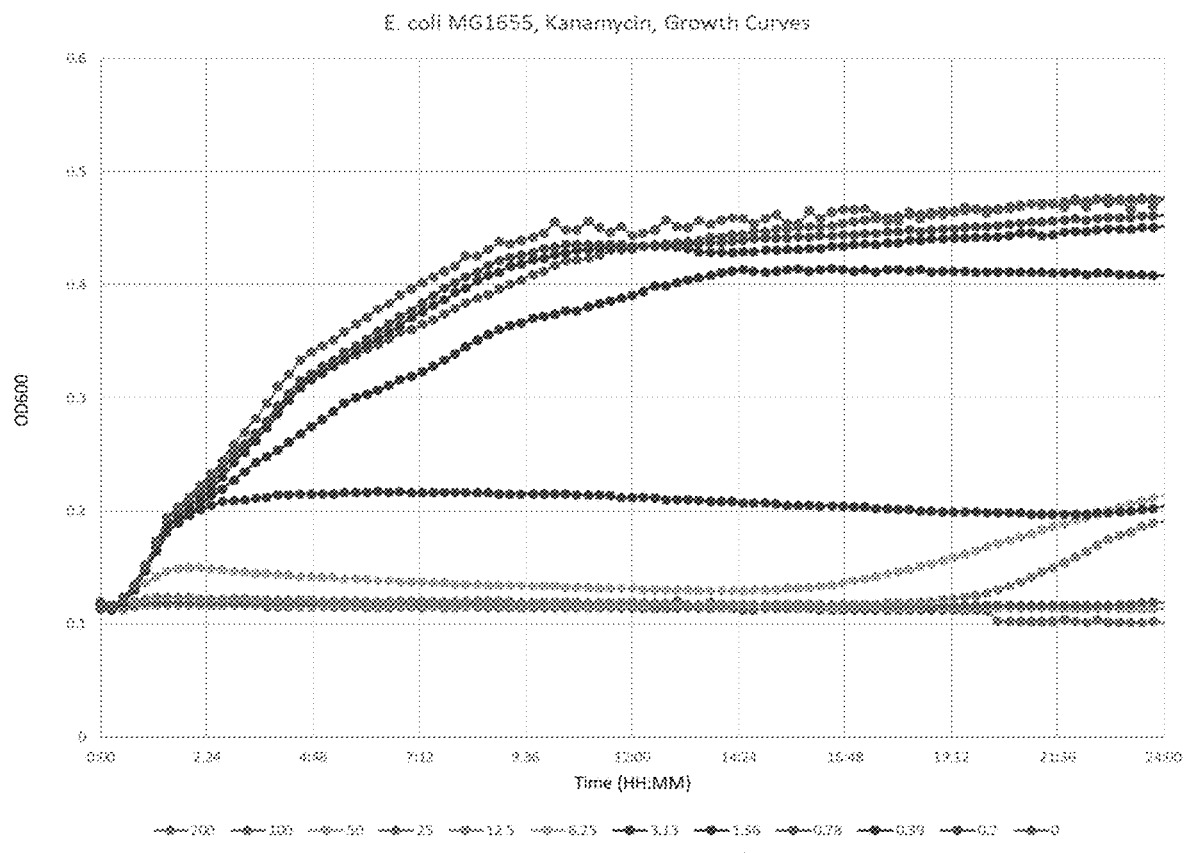
FIG. 17 shows growth curve analysis of *E. coli* MG1655 cultures exposed to varying dose of kanamycin, as measured by optical density at 600 nm (OD600). 25 μg/ml is the minimum concentration that completely blocked growth over the full 24 hr culture time. Similar results were obtained with TOP10 and DH5α strains.

FIGS. 16A-16B show results for growth curve analysis of *E. coli* MG1655 to varying doses of ampicillin. FIG. 17 shows growth curve analysis for strain MG1655 without plasmid in the presence of varying concentrations of kanamycin. To ensure antibiotic effects were as pronounced and rapid as possible, the highest concentration (200 μg/ml) kanamycin was used in the initial sensor test experiments described below.

Since kanamycin acts by inhibiting protein synthesis rather than directly lysing bacterial cells, the exposure duration to yield a detectable change with *E. coli* was uncertain. To determine the effect of rapid complete lysis of bacteria on the sensor surface, sodium hydroxide was added at final concentration 1M. Complete lysis under these conditions was verified by phase contrast microscopy.

Figure 18A:
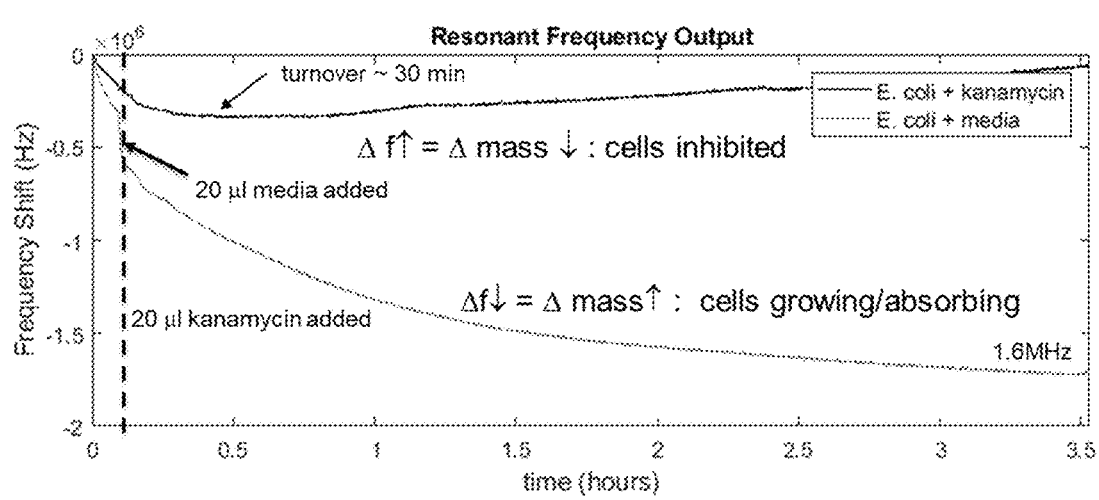
FIGS. 18A-18B show results of assays conducted with an acoustic wave sensor system including an active shunt capacitance cancelling oscillator circuit. Provided are measured frequency shifts (A,B) for *E. coli* cells in the presence of an antibiotic (kanamycin, black), as compared to control (exposure to media, gray).
Figure 18B:
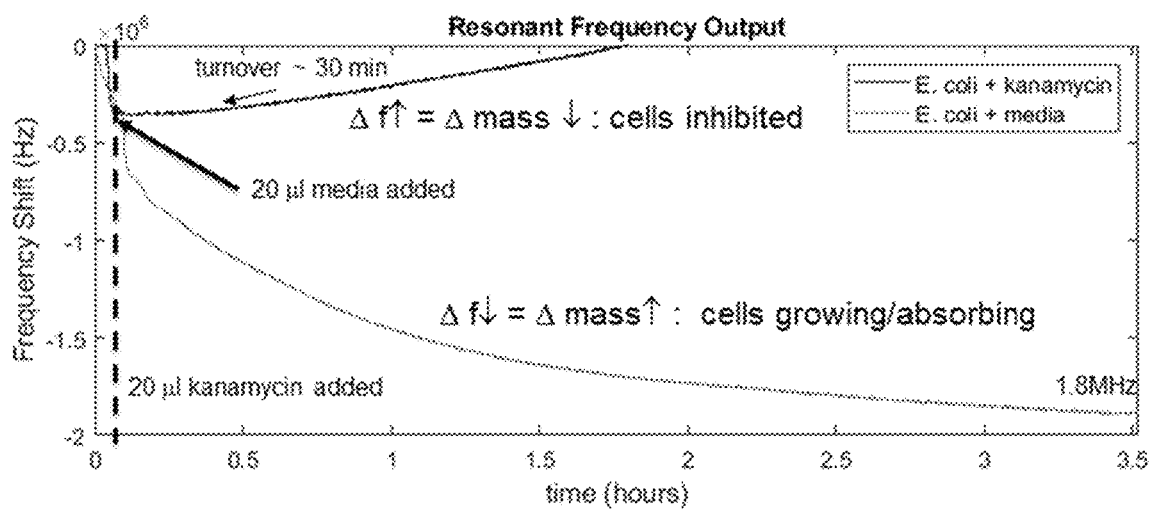

The sensitivity of *E. coli* TOP10 to kanamycin was measured using the 36YLT SH-LSAW sensors which have a resonate frequency of ~85 MHz. In the assay, a sample of *E. coli* TOP10 was prepared at undiluted concentrations consisting of approximately $10^7$ cfu/ml. Kanamycin was prepared at 15×(375 μg/ml) in Tris-buffered saline. FIG. 18A shows the time-response of adding kanamycin to *E. coli* in the fluidic cell. At t=0, the fluidic cell was filled with *E. coli* and media. In the absence of kanamycin, the *E. coli* is expected to steadily absorb and grow on the surface of the resonators, causing the resonant frequency to decrease. In FIG. 18B, the results indicate a similar trend, except the resonant frequency steadily increases beyond the starting frequency shift of '0', indicating that the top surface of the sensor is lifting off into solution. However, the results indicate that *E. coli* ($10^8$ cells/ml) in the presence of kanamycin are not able to adhere, where the turnover time is 30 min to 60 min. Pre-plating the bacteria to the surface of the acoustic resonators would reduce the amount of bacteria required in the samples.

Overall, we demonstrate that acoustic resonators (sensors) can be used to detect antibiotic resistance of bacteria (e.g., *E. coli*) on a shorter time-scale than other growth based methods. In addition, a new monitoring method was created that enables removal of the shunt capacitance from the resonators. This method is called active shunt capacitance cancelling oscillator (ASCCO), which tracks the true acoustic series resonance and damping of the resonator unlike other methods. Since the method avoids impedance distortion and phase shift problems associated with non-zero shunt capacitance, it is valuable for sensor applications. SH- LSAW sensors using ST-Quartz and 36YLT substrates were developed for air and liquid based measurements. These sensors had a resonant frequency of 85 MHz to 100 MHz. The use of dense metal electrodes supported the excitation of SH-LSAW acoustic waves, creating very compact sensors. The ST-90° X resonators were used to develop the ASCCO circuit. However, since the electromechanical coupling of ST-90° X is small, liquid damping was excessive and prevented operation in water. In contrast, the electromechanical coupling of 36YLT is 46× larger and thus suitable for liquid phase sensing. Measurements showed that the adsorption of E. coli to the sensors was inhibited by the presence of kanamycin when used in a growth/absorbing based assay.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A system comprising:
an active resonator comprising a first piezoelectric substrate having a top surface;
an electrode region disposed on the top surface of the first piezoelectric substrate, wherein the electrode region is configured to launch a shear horizontal surface acoustic wave and to detect the acoustic wave transmitted through the substrate;
an inactive resonator comprising a second piezoelectric substrate, wherein the first piezoelectric substrate is configured to propagate the shear horizontal surface acoustic wave and the second piezoelectric substrate is configured to propagate an out-of-band acoustic mode, as compared to an acoustic mode comprising the shear horizontal surface acoustic wave; and
an active shunt capacitance cancelling oscillator circuit that comprises:
an amplifier comprising an amplifier input and an amplifier output;
a first transistor connected between the active resonator and the amplifier output; and
a current mirror connected between the first transistor and the amplifier input, wherein the current mirror is configured to provide a current component controlled by a capacitance of the inactive resonator, thereby effectively cancelling out a shunt capacitance associated with the active resonator.

2. The system of claim 1, further comprising:
one or more reflector regions disposed on the top surface of the first piezoelectric substrate and disposed outside of a periphery of the electrode region, wherein the one or more reflector regions are configured to provide an acoustic cavity disposed within the first piezoelectric substrate, and wherein the acoustic cavity is configured to store mechanical energy from the acoustic wave;
an optional guide layer overlying the top surface of the first piezoelectric substrate, the electrode region, and the one or more reflector regions, or portions thereof, in which a shear velocity in the guide layer is less than a shear velocity in the first piezoelectric substrate; and
a functionalized active area disposed in proximity to the acoustic cavity.

3. The system of claim 2, wherein the functionalized active area comprises a plurality of immobilized cells.

4. The system of claim 2, wherein the functionalized active area comprises a plurality of capture agents configured to bind to or interact with one or more targets.

5. The system of claim 2, further comprising a fluidics module configured to be in fluidic communication with the functionalized active layer.

6. The system of claim 1, wherein each of the first piezoelectric substrate and the second piezoelectric substrate comprises the same material.

7. The system of claim 1, wherein the inactive resonator further comprises:
a second electrode region disposed on a top surface of the second piezoelectric substrate, wherein the second electrode region is configured to minimize launching of a shear horizontal surface acoustic wave through the second piezoelectric substrate.

8. The system of claim 1, wherein the first piezoelectric substrate and the second piezoelectric substrate comprise lithium tantalate, lithium niobate, potassium niobate, or quartz.

9. A system comprising:
an active resonator comprising a first piezoelectric substrate, where the first piezoelectric substrate has a first crystal orientation such that first acoustic waves that propagate from the first piezoelectric substrate travel in a first direction;
an inactive resonator comprising a second piezoelectric substrate, where the second piezoelectric substrate has a second crystal orientation that differs from the first crystal orientation of the first piezoelectric substrate such that second acoustic waves that propagate from the second piezoelectric substrate travel in a second direction that differs from the first direction;
an amplifier comprising an amplifier input and an amplifier output;
a first transistor connected between the active resonator and the amplifier output; and
a first current mirror connected between the first transistor and the amplifier input, wherein the first current mirror is configured to provide a current component controlled by a capacitance of the inactive resonator, thereby effectively cancelling out a shunt capacitance associated with the active resonator.

10. The system of claim 9, wherein the amplifier is a limiting amplifier.

11. The system of claim 9, wherein each of the active resonator and the inactive resonator comprises an electrode region and one or more reflector regions disposed on the top surfaces of the first piezoelectric substrate and the second piezoelectric substrate, respectively.

12. The system of claim 11, wherein the one or more reflector regions of the active resonator are configured to provide an acoustic cavity disposed within the first piezoelectric substrate, and wherein the acoustic cavity is configured to store mechanical energy from the first acoustic waves.

13. The system of claim 12, further comprising a functionalized active area disposed in proximity to the acoustic cavity of the active resonator.

14. The system of claim 13, wherein the functionalized active area comprises a plurality of immobilized cells.

15. The system of claim 13, wherein the functionalized active area comprises a plurality of capture agents configured to bind one or more targets.

16. The system of claim 9, further comprising:
a tank circuit connected between ground and the amplifier input, wherein the tank circuit comprises an inductor, a capacitor, and a resistor.

17. The system of claim 9, further comprising:
a second transistor connected between the inactive resonator and the amplifier output; and
a second current mirror connected between the first transistor and the second transistor.

18. A system comprising:
an active resonator comprising a first piezoelectric substrate, where the first active resonator has a first acoustic mode;
an inactive resonator comprising a second piezoelectric substrate, where the inactive resonator has a second acoustic mode that is separable from the first acoustic mode of the active resonator;
an amplifier comprising an amplifier input and an amplifier output;
a first transistor having an input connected to the amplifier output and a non-inverting output connected to the active resonator;
a first current mirror connected between an inverting output of the first transistor and the amplifier input;
a second transistor having an input connected to the amplifier output and a non-inverting output connected to the inactive resonator; and
a second current mirror connected between an inverting output of the second transistor and the inverting output of the first transistor, wherein the first current mirror and the second current mirror are configured to provide a current component controlled by a capacitance of the inactive resonator, thereby effectively cancelling out a shunt capacitance associated with the active resonator.

19. The system of claim 18, further comprising:
a tank circuit connected between ground and the amplifier input, wherein the tank circuit comprises an inductor, a capacitor, and a resistor.

20. The system of claim 18, wherein each of the active resonator and the inactive resonator comprises an electrode region and one or more reflector regions disposed on top surfaces of the first piezoelectric substrate and the second piezoelectric substrate, respectively.

21. The system of claim 20, wherein the one or more reflector regions of the active resonator are configured to provide an acoustic cavity disposed within the first piezoelectric substrate, and wherein the acoustic cavity is configured to store mechanical energy from an acoustic wave.

22. The system of claim 21, further comprising a functionalized active area disposed in proximity to the acoustic cavity of the active resonator.

23. The system of claim 22, wherein the functionalized active area comprises a plurality of immobilized cells.

24. The system of claim 22, wherein the functionalized active area comprises a plurality of capture agents configured to bind to or interact with one or more targets.

\* \* \* \* \*